United States Patent
Oda et al.

(10) Patent No.: US 6,662,121 B1
(45) Date of Patent: Dec. 9, 2003

(54) THERMAL FLUID SENSOR, FLUID DISCRIMINATING APPARATUS AND METHOD, FLOW SENSOR, AND FLOW RATE MEASURING APPARATUS AND METHOD

(75) Inventors: Seiji Oda, Shizuoka (JP); Michiaki Yamaura, Shizuoka (JP)

(73) Assignee: Yazaki Corporation, Tokyo (JP)

( * ) Notice: Subject to any disclaimer, the term of this patent is extended or adjusted under 35 U.S.C. 154(b) by 0 days.

(21) Appl. No.: 09/720,473

(22) PCT Filed: Apr. 25, 2000

(86) PCT No.: PCT/JP00/02688
§ 371 (c)(1),
(2), (4) Date: Feb. 13, 2001

(87) PCT Pub. No.: WO00/65315
PCT Pub. Date: Nov. 2, 2000

(30) Foreign Application Priority Data

Apr. 27, 1999 (JP) .......................................... 11-120614
Mar. 30, 2000 (JP) ....................................... 2000-94437

(51) Int. Cl.⁷ ............................................. G01F 1/68
(52) U.S. Cl. ................... 702/45; 73/204.18; 73/204.26; 374/30; 392/470; 422/51; 422/52; 702/113
(58) Field of Search .............................. 702/45, 12, 13, 702/14, 50, 51, 52, 100, 114; 73/204.11–204.27; 392/470; 422/51, 52; 700/281

(56) References Cited

U.S. PATENT DOCUMENTS

| 3,891,391 A | * | 6/1975 | Boone ...................... 73/204.18 |
| 4,944,035 A | * | 7/1990 | Aagardl et al. ................ 374/30 |
| 5,217,690 A | * | 6/1993 | Mudd et al. ................... 422/51 |
| 5,321,983 A | * | 6/1994 | Nagata ..................... 73/204.18 |
| 5,515,295 A | * | 5/1996 | Wang .......................... 702/113 |
| 5,703,288 A | * | 12/1997 | Horiguchi et al. ....... 73/204.26 |
| 6,175,688 B1 | * | 1/2001 | Cassidy et al. ............. 392/470 |

FOREIGN PATENT DOCUMENTS

| JP | 5-107093 | | 4/1993 |
| JP | 05-107093 | * | 4/1993 |
| JP | 8-110317 | | 4/1996 |
| JP | 9-89619 | | 4/1997 |

OTHER PUBLICATIONS

IEEE Standard Dictionary of Electrical and Electronics Terms 6ᵗʰ edition. p. 173.*

* cited by examiner

Primary Examiner—John Barlow
Assistant Examiner—John Le
(74) Attorney, Agent, or Firm—Armstrong, Westerman & Hattori, LLP

(57) ABSTRACT

When a micro-heater heats fluid using an external driving current, an upstream thermopile 8 detects the temperature of the fluid before it is heated to produce a first temperature detected signal and a downstream thermopile 9 detects the temperature of the fluid before it is heated to produce a second temperature detected signal. The flow rate is computed based on the difference signal between both detected signals. A right thermopile 11 and a left thermopile 13, which are arranged in a direction orthogonal to the flow direction of the fluid, detect the temperature of the fluid to produce a right temperature detected signal and a left temperature detected signal. The property of the fluid is computed on these right and left temperature detected signals. The flow rate is corrected on the basis of the property thus computed. The flow rate of an object fluid for measurement can be accurately measured by a flow sensor whose output characteristic varies when the kind or composition of the fluid changes.

48 Claims, 6 Drawing Sheets

THERMAL FLUID SENSOR, FLUID DISCRIMINATING APPARATUS AND METHOD, FLOW SENSOR, AND FLOW RATE MEASURING APPARATUS AND METHOD

TECHNICAL FIELD

This invention relates to a thermal fluid sensor which can be used to discriminate the kind of fluid, a fluid identifying apparatus and method for identifying the kind of an object fluid for measurement (simply referred to as object fluid or fluid) on the basis of a temperature detected signal produced from the fluid sensor, a flow velocity sensor (simply referred to as a flow sensor) which can be used for measurement of the flow rate, and a flow rate measuring apparatus and method for measuring the flow rate of the object fluid on the basis of a temperature detected signal. More particularly, this invention relates to a flow sensor and a flow rate measuring apparatus and method which can measure the flow rate of the fluid accurately even when the kind and composition of the fluid are changed, and relates to a flow rate measuring apparatus and method which can measure the flow rate of the fluid even when the measuring range of the flow rate is relatively wide.

BACKGROUND ART

FIG. 9 shows an arrangement view of a conventional thermal micro-flow sensor. A micro-flow sensor 101 includes an Si substrate 102, a diaphragm 103, a micro-heater 104, a downstream thermopile 105 formed on the diaphragm 103 at the lower end of the micro-heater 104, power source terminals 106A, 106B for supplying a driving current to the micro-heater 104, an upstream thermopile 108 formed on the diaphragm 103 at the upper end of the micro-heater 104, first output terminals 109A, 109B for producing a first temperature detected signal supplied from the upstream thermopile 108, and second output terminals 107A, 107B for producing a second temperature detected signal supplied from the downstream thermopile 105.

According to the micro-flow sensor 101 thus configured, in response to the driving current supplied externally, the micro-heater 104 heats an object fluid for measurement such as a gas to generate uniform temperature distributions from itself to the downstream thermopile 105 and from itself to the upstream thermopile 108.

In this state, when the flow from P to Q is generated in the object fluid such the gas, the temperature distribution around the micro-heater is deflected downstream of the object fluid, i.e. toward the downstream thermopile 105. Therefore, the upstream thermopile 108 detects the temperature lower than when no flow is generated in the fluid, i.e. flow rate=0. Then, the upstream thermopile 108 produces the first temperature detected signal corresponding to the detected temperature.

On the other hand, the downstream thermopile 105 detects the temperature higher than when no flow is generated in the fluid, i.e. flow rate=0 by the degree the temperature distribution has been deflected downstream. Then, the downstream thermopile 105 produces the second temperature detected signal corresponding to the detected temperature. Thus, a flow rate measuring apparatus (not shown) can measure the flow rate of the object fluid on the basis of a difference signal between the first temperature detected signal from the upstream thermopile 108 and the second temperature detected signal from the downstream thermopile 105.

However, the conventional micro-flow sensor as shown in FIG. 9 has a disadvantage that when the kind or composition of the object fluid, the output characteristic is also changed.

Specifically, when the kind or composition of the fluid, the physical property (hereinafter simply referred to as "property") of the fluid such as thermal conductivity, specific heat, viscosity, density, etc. is also changed. This modifies the temperature distribution of the fluid heated by the micro-heater, and hence the output characteristic.

In order to obviate such failure, aside from the micro-flow sensor, a gas analysis sensor was arranged, or otherwise the micro-flow sensor or a device incorporating it was caused to recognize the properties of the fluid previously.

However, for example, in a gas meter, the gas having the same standard has a slightly different composition of the raw gas according to various lots. The gas composition for controlling the quantity of heat is adjusted with limited accuracy by a gas production factory so that the composition of the gas having the same standard may be changed. Therefore, there was a limit for the characteristic value of the fluid to be previously recognized by the micro-flow sensor and the device incorporating it.

Where the gas analysis sensor is arranged aside, the gas meter is upsized, and the method for correcting the flow rate and the location of the gas analysis sensor must be considered. This makes it difficult to manufacture the gas meter at low cost.

DISCLOSURE OF THE INVENTION

This invention has been accomplished in view of the above circumstance.

An object of this invention is to provide a thermal fluid sensor and fluid identifying apparatus and method which permits a flow sensor to measure the flow rate of an object fluid accurately even when the flow sensor produces a change in the output characteristic with a change in the kind or composition of an object fluid, and also provide the flow sensor and flow rate measuring apparatus and method which is preferably used to measure the flow rate using these thermal fluid sensor and fluid identifying apparatus and method.

In order to attain the above objects, the thermal fluid sensor defined in another aspect of the invention is characterized by comprising:

a heater for heating an object fluid for measurement flowing through a flow path by a driving current externally supplied;

a side temperature sensor arranged in a direction orthogonal to the flow direction of the object fluid with respect to the heater to detect the temperature of the object fluid so that a temperature detected signal is produced; and a supporting board for supporting the heater and the side temperature sensor.

The fluid discriminating apparatus in another aspect of the invention for discriminating the kind of the object fluid using the thermal fluid sensor is further characterized by comprising:

fluid property computing means for computing the property of the object fluid on the basis of the temperature detected signal supplied from the side temperature sensor in the thermal fluid sensor.

The fluid discriminating apparatus in another aspect of the invention for discriminating the kind of the object fluid using the thermal fluid sensor is further characterized by comprising:

flow rate measuring means for measuring the flow rate of the object fluid flowing through the fluid path;

reference range data storage means for storing data of a plurality of kinds of reference ranges of the temperature detected signal corresponding to the flow rates of the object fluid flowing through the flow path, the reference ranges being different according to the kinds of the object fluid and correlated with the kinds;

reference range data inferring means for inferring a single reference range data corresponding to the flow rate of the object fluid from data of the plurality of reference ranges stored in the reference range data storage means;

pertinent reference range determining means for determining the reference range correlated with the object fluid to which the temperature detected signal belongs, wherein it is determined that the object fluid correlated with the reference range thus determined is the object fluid flowing through the flow path.

The fluid discriminating method in another aspect of the invention of discriminating the object fluid using the thermal fluid sensor is further characterized by comprising:

fluid-property computing step of computing the property of the object fluid on the basis of the temperature detected signal supplied from the side temperature sensor in the thermal fluid sensor.

The fluid discriminating method in another aspect of the invention for discriminating the kind of the object fluid using the thermal fluid sensor, comprises:

flow rate measuring step of measuring the flow rate of the object fluid flowing through the fluid path;

reference range data inferring means step of inferring a single reference range data corresponding to the flow rate of the object fluid from a group of data of a plurality of prescribed reference ranges of the temperature detected signal corresponding to the flow rates of the object fluid flowing through the flow path, the reference ranges being different according to the kinds of the object fluid and correlated with the kinds;

pertinent reference range determining step of determining the reference range correlated with the object fluid to which the temperature detected signal belongs, wherein it is determined that the object fluid correlated with the reference range thus determined is the object fluid flowing through the flow path.

The flow rate measuring apparatus in another aspect of the invention for measuring the flow rate of the object fluid flowing through the flow path using the thermal fluid sensor is further characterized by comprising:

flow rate measuring means for measuring the flow rate of the object fluid flowing through the flow path; and flow rate correcting means for correcting the flow rate of the fluid measured by the flow rate measuring means.

The flow rate measuring apparatus in another aspect of the invention for measuring the flow rate of the object fluid flowing through the flow path using the thermal fluid sensor is further characterized by comprising:

flow rate measuring means for measuring the flow rate of the object fluid flowing through the flow path;

deciding means for deciding whether the flow rate of the fluid measured by the flow rate measuring means is in a high flow rate state or a low flow rate;

flow rate outputting means for outputting an output signal from the flow rate measuring means as a flow rate detected signal as it is if the flow rate is decided to be in the low flow rate state, and another output signal when the output signal from the flow rate measuring means is divided by the temperature detected signal from the side temperature sensor if the flow rate is decided to be in the high flow rate state.

The flow rate measuring apparatus in another aspect of the invention for measuring the flow rate of the object fluid flowing through the flow path using the thermal fluid sensor, flow rate measuring means for measuring the flow rate of the fluid flowing through the flow path and producing an output signal having a value corresponding to the flow rate thus measured;

fluid property computing means for computing the property of the object fluid on the basis of the temperature detected signal supplied from the side temperature sensor in the thermal fluid sensor;

parameter storage means storing a plurality of kinds of parameters each for converting the output signal from the flow rate measuring means into a flow rate; and selecting means for selecting a single parameter of the plurality of kinds of parameters stored in the parameter storage means on the basis of the property of the object fluid computed by the fluid property computing means, wherein the flow rate converted from the output signal from the flow rate measuring means using the single parameter selected by the selecting means is taken as the measured value of the flow rate of the object fluid flowing through the flow path.

The flow rate measuring method in another aspect of the invention for measuring the flow rate of the object fluid flowing through the flow path using the thermal fluid sensor, is further characterized by comprising:

flow rate measuring step of measuring the flow rate of the object fluid flowing through the flow path; and flow rate correcting step of correcting the flow rate of the fluid measured by the flow rate measuring means.

The flow rate measuring apparatus in another aspect of the invention for measuring the flow rate of the object fluid flowing through the flow path using the thermal fluid sensor is further characterized by comprising:

flow rate measuring step of measuring the flow rate of the object fluid flowing through the flow path;

deciding step of deciding whether the flow rate of the fluid measured by the flow rate measuring means is in a high flow rate state or a low flow rate;

flow rate outputting step of outputting an output signal acquired in the flow rate measuring step as a flow rate detected signal as it is if the flow rate is decided to be in the low flow rate state, and another output signal when the output signal acquired in the flow rate measuring step is divided by the temperature detected signal from the side temperature sensor if the flow rate is decided to be in the high flow rate state.

The flow rate measuring method in another aspect of the invention for measuring the flow rate of the object fluid flowing through the flow path using the thermal fluid sensor flow rate measuring step of measuring the flow rate of the fluid flowing through the flow path and producing an output signal having a value corresponding to the flow rate thus measured;

fluid property computing step of computing the property of the object fluid on the basis of the temperature detected signal supplied from the side temperature sensor in the thermal fluid sensor;

selecting means for selecting a single parameter of the plurality of kinds of prescribed parameters on the basis of the property of the object fluid computed in the fluid property computing step, the plurality of kinds of parameters each for converting the output signal from the flow rate measuring means into a flow rate, wherein the flow rate converted from the output signal from the flow rate measuring means using the single parameter selected in the selecting step is taken as the measured value of the flow rate of the object fluid flowing through the flow path.

The flow sensor defined in another aspect of the invention is characterized by comprising:

a heater for heating an object fluid flowing through a flow path by a driving current externally supplied;

an upstream temperature sensor arranged upstream of the object fluid with respect to the heater to detect the temperature of the object fluid so that a first temperature detected signal is produced;

a downstream temperature sensor arranged downstream of the object fluid with respect to the heater to detect the temperature of the object fluid so that a second temperature detected signal is produced;

a side temperature sensor arranged in a direction orthogonal to the flow direction of the object fluid with respect to the heater to detect the temperature of the object fluid so that a third temperature detected signal is produced; and a supporting board for supporting the heater, the upstream sensor, the downstream sensor and the side temperature sensor.

The fluid discriminating apparatus in another aspect of the invention for discriminating the kind of the object fluid using the thermal fluid sensor is further characterized by comprising:

flow rate measuring means for measuring a flow rate of the object fluid on the basis of a difference signal between the first temperature detected signal supplied from the upstream temperature sensor and the second temperature detected signal supplied from the downstream temperature sensor;

reference value storage means for storing a plurality of kinds of reference values of the third temperature detected signal supplied from the side temperature sensor within the flow sensor, the reference values corresponding to flow rates of the object fluid flowing through the flow path;

reference value inferring means for inferring a single reference value corresponding to the flow rate of the object fluid measured by the flow rate measuring means from the plurality of kinds of reference values stored in the reference value storage means; and temperature detected signal ratio computing means for computing a ratio of the reference value inferred by the reference value inferring means to the third temperature detected signal supplied from the side temperature sensor, wherein the fluid property computing means computes the property of the object fluid on the basis of the ratio computed by the temperature detected signal ratio computing means.

The fluid discriminating apparatus defined in another aspect of the invention is characterized by comprising:

flow rate measuring means for measuring a flow rate of the object fluid on the basis of a difference signal between the first temperature detected signal supplied from the upstream temperature sensor and the second temperature detected signal supplied from the downstream temperature sensor; and fluid property computing means for multiplying the flow rate or its square root of the object fluid flowing through the flow path measured by the flow rate measuring means by the temperature detected signal supplied from the side temperature sensor in the flow sensor, thereby acquiring the property of the object fluid.

The fluid discriminating apparatus in another aspect of the invention for discriminating the kind of the object fluid using the flow sensor is further characterized by comprising:

flow rate measuring means for measuring a flow rate of the object fluid on the basis of a difference signal between the first temperature detected signal supplied from the upstream temperature sensor and the second temperature detected signal supplied from the downstream temperature sensor; and reference range data storage means for storing data of a plurality of kinds of reference ranges of the third temperature detected signal corresponding flow rates of the object fluid flowing through the flow path, the reference ranges being different according to the kinds of the object fluid and correlated with the kinds;

reference range data inferring means for inferring a single reference range data corresponding to the flow rate of the object fluid from data of the plurality of reference ranges stored in the reference range data storage means;

pertinent reference range determining means for determining the reference range correlated with the object fluid to which the third temperature detected signal belongs, wherein it is determined that the object fluid correlated with the reference range thus determined is the object fluid flowing through the flow path.

The fluid discriminating method in another aspect of the invention for discriminating the kind of the object fluid using the flow sensor is further characterized by comprising;

flow rate measuring step of measuring a flow rate of the object fluid on the basis of a difference signal between the first temperature detected signal supplied from the upstream temperature sensor and the second temperature detected signal supplied from the downstream temperature sensor;

reference value storage step of storing a plurality of kinds of reference values of the third temperature detected signal supplied from the side temperature sensor within the flow sensor, the reference values corresponding to flow rates of the object fluid flowing through the flow path;

reference value inferring step of inferring a single reference value corresponding to the flow rate of the object fluid measured by the flow rate measuring means from the plurality of kinds of reference values stored in the reference value storage means; and temperature detected signal ratio computing step of computing a ratio of the reference value inferred by the reference value inferring means to the third temperature detected signal supplied from the side temperature sensor, wherein the fluid property computing means computes the property of the object fluid on the basis of the ratio computed by the temperature detected signal ratio computing means.

The fluid discriminating method in another aspect of the invention for discriminating the kind of the object fluid using the flow sensor, flow rate measuring step for computing a flow rate of the object fluid on the basis of a difference signal between the first temperature detected signal supplied from the upstream temperature sensor and the second temperature detected signal supplied from the downstream temperature sensor; and fluid property computing step of multiplying the flow rate or its square root of the object fluid flowing through the flow path measured by the flow rate measuring means by the temperature detected signal supplied from the side temperature sensor in the flow sensor, thereby acquiring the property of the object fluid.

The fluid discriminating method in another aspect of the invention discriminating the kind of the object fluid using the flow sensor is further characterized by comprising:

flow rate measuring step of measuring a flow rate of the object fluid on the basis of a difference signal between the first temperature detected signal supplied from the upstream temperature sensor and the second temperature detected signal supplied from the downstream temperature sensor; and reference range data inferring step of inferring a single reference range data corresponding to the flow rate of the object fluid from data of a plurality kinds of reference ranges of the third temperature detected signal corresponding to the flow rates of the object fluid flowing through the flow path, the reference ranges being different according to the kinds of the object fluid and correlated with the kinds;

pertinent reference range determining step of determining the reference range correlated with the object fluid to which the third temperature detected signal belongs, wherein it is determined that the object fluid correlated with the reference range thus determined is the object fluid flowing through the flow path.

The flow rate measuring apparatus in another aspect of the invention for measuring the flow rate of the object fluid flowing through the flow path using the flow sensor, comprises:

flow rate computing means computing a flow rate of the object fluid on the basis of a difference signal between the first temperature detected signal supplied from the upstream temperature sensor and the second temperature detected signal supplied from the downstream temperature sensor; and fluid property computing means for computing the property of the object fluid on the basis of the third temperature detected signal supplied from the side temperature sensor with the flow sensor; and flow rate correcting means for correcting the flow rate of the object fluid computed by the flow rate computing means on the basis of the property of the object fluid computed by the fluid property computing means.

The flow rate measuring apparatus defined in claim 41 for measuring the flow rate of the object fluid flowing through the flow path using the flow sensor set forth in claim 24 is characterized by comprising:

flow rate computing means for computing a flow rate of the object fluid on the basis of a difference signal between the first temperature detected signal supplied from the upstream temperature sensor and the second temperature detected signal supplied from the downstream temperature sensor; and deciding means for deciding whether the flow rate of the fluid measured by the flow rate measuring means is in a high flow rate state or a low flow rate;

flow rate outputting means for outputting an output signal from the flow rate measuring means as a flow rate detected signal as it is if the flow rate is decided to be in the low flow rate state, and another output signal when the output signal from the flow rate measuring means is divided by the third temperature detected signal from the side temperature sensor if the flow rate is decided to be in the high flow rate state.

The flow rate measuring apparatus defined in claim 42 for measuring the flow rate of the object fluid flowing through the flow path using the flow sensor set forth in claim 24, flow rate computing means for computing a flow rate of the object fluid on the basis of a difference signal between the first temperature detected signal supplied from the upstream temperature sensor and the second temperature detected signal supplied from the downstream temperature sensor and producing an output signal having a value corresponding to the flow rate thus computed;

fluid property computing means for computing the property of the object fluid on the basis of the third temperature detected signal supplied from the side temperature sensor in the flow sensor;

parameter storage means storing a plurality of kinds of parameters each for converting the output signal from the flow rate computing means into a flow rate; and selecting means for selecting a single parameter of the plurality of kinds of parameters stored in the parameter storage means on the basis of the property of the object fluid computed by the fluid property computing means, wherein the flow rate converted from the output signal from the flow rate measuring means using the single parameter selected by the selecting means is taken as the measured value of the flow rate of the object fluid flowing through the flow path.

The flow rate measuring method defined in claim 43 for measuring the flow rate of the object fluid flowing through the flow path using the flow sensor set forth in claim 24 is characterized by comprising:

flow rate computing step of computing a flow rate of the object fluid on the basis of a difference signal between the first temperature detected signal supplied from the upstream temperature sensor and the second temperature detected signal supplied from the downstream temperature sensor; and fluid property computing step of computing the property of the object fluid on the basis of the third temperature detected signal supplied from the side temperature sensor within the flow sensor;

flow rate correcting step of correcting the flow rate of the object fluid computed by the flow rate computing means on the basis of the property of the object fluid computed in the fluid property computing step.

The flow rate measuring apparatus defined in claim 45 for measuring the flow rate of the object fluid flowing through the flow path using the flow sensor set forth in claim 24, comprising:

flow rate computing step for computing a flow rate of the object fluid on the basis of a difference signal between the first temperature detected signal supplied from the upstream temperature sensor and the second temperature detected signal supplied from the downstream temperature sensor, thereby acquiring a signal having the value corresponding to the computed flow rate; and deciding means for deciding whether the flow rate of the fluid acquired in the flow rate measuring step is in a high flow rate state or a low flow rate;

flow rate outputting means for outputting an output signal acquired in the flow rate computing step as a flow rate detected signal as it is if the flow rate is decided to be in the low flow rate state, and another output signal when the output signal acquired in the flow rate computing step is divided by the third temperature detected signal from the side temperature sensor if the flow rate is decided to be in the high flow rate state.

The flow rate measuring apparatus in another aspect of the invention for measuring the flow rate of the object fluid flowing through the flow path using the flow sensor is further characterized by comprising:

flow rate computing step of computing a flow rate of the object fluid on the basis of a difference signal between the first temperature detected signal supplied from the upstream temperature sensor and the second temperature detected signal supplied from the downstream temperature sensor and producing an output signal having a value corresponding to the flow rate thus computed;

fluid property computing step of computing the property of the object fluid on the basis of the third temperature detected signal supplied from the side temperature sensor in the flow sensor;

parameter storage means storing a plurality of kinds of parameters each for converting the output signal acquired in the flow rate computing step into a flow rate; and selecting step of selecting a single parameter of the plurality of kinds of parameters on the basis of the property of the object fluid computed in the fluid property computing step, wherein the flow rate converted from the output signal from the flow rate computing step using the single parameter selected in the selecting step is taken as the measured value of the flow rate of the object fluid flowing through the flow path.

BEST MODE FOR CARRYING OUT THE INVENTION

Concrete Configuration of the micro-flow sensor according to a first preferred embodiment of this invention Now referring to FIGS. 1 and 2, an explanation will be given of the configuration of the micro-flow sensor according to the first embodiment of this invention.

Figure 1:
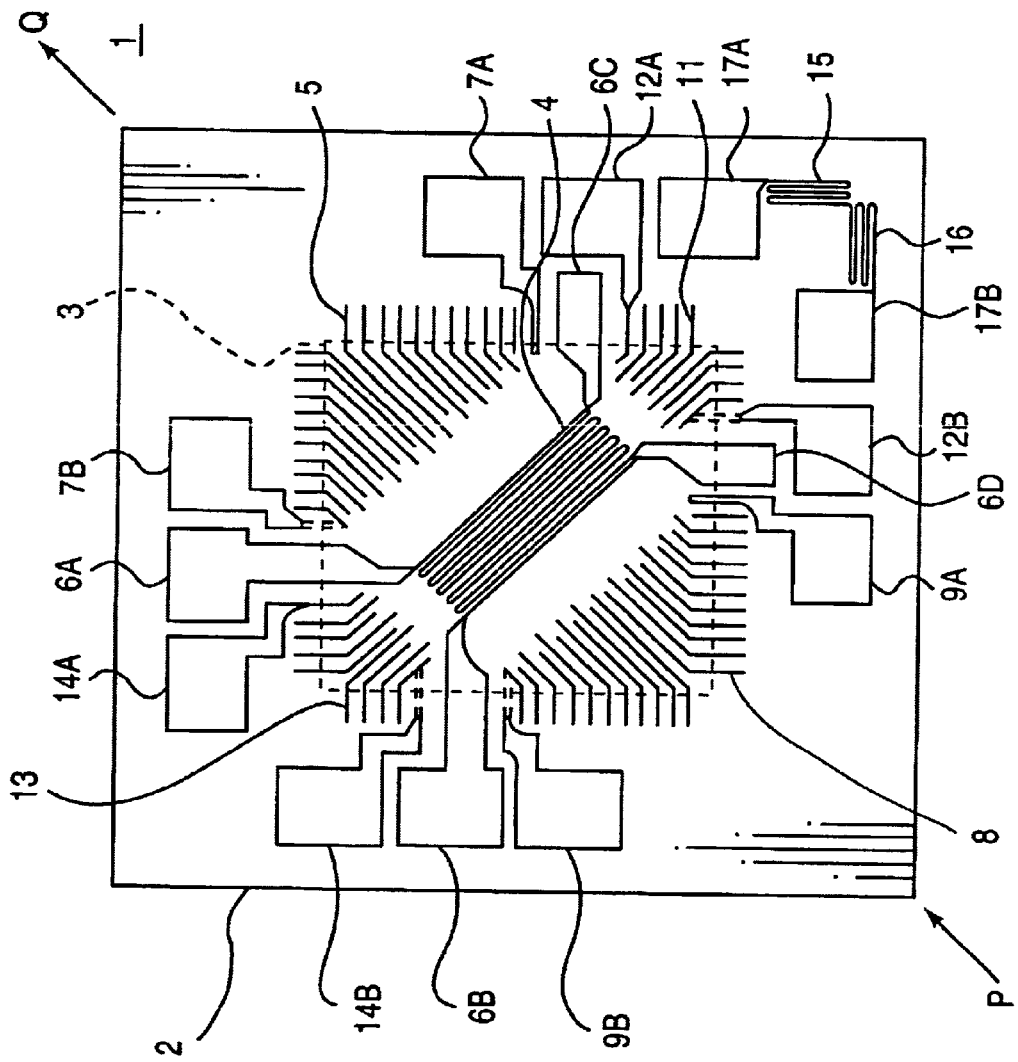
FIG. 1 is a view showing a configuration of the micro-flow sensor according to a first embodiment of this invention.

As seen from FIG. 1, a micro-flow sensor, generally 1, includes a Si board 2, a diaphragm 3, a micro-heater 4 of Pt formed on the diaphragm 2, a downstream thermopile 5 formed downstream of the micro-heater 4 on the diaphragm 3, power source terminals 6A, 6B for supplying a driving current to the micro-heater 4 from a power source (not shown), an upstream thermopile 8 formed upstream of the micro-heater 4 on the diaphragm 3, first output terminals 9A, 9B for producing a first temperature detected signal supplied from the upstream thermopile 8, and second output terminals 7A, 7B for producing a second temperature detected signal supplied from the downstream thermopile 5.

The micro-flow sensor 1 further includes a right thermopile 11, third output terminals 12A, 12B, a left thermopile 13 and fourth output terminals 14A, 14B. The right thermopile 11 is arranged in a direction orthogonal to the flow direction (direction from P to Q) of fluid with respect to the micro-heater 4 and serves to detect the property to produce a right temperature detected signal (corresponding to a third temperature detected signal). The third output terminals 12A, 12B provide the right temperature detected signal produced from the right thermopile 11. The left thermopile 13 is arranged in a direction orthogonal to the flow direction of fluid with respect to the micro-heater 4 and serves to detect the property to produce a left temperature detected signal (corresponding to a third temperature detected signal). The fourth output terminals 14A, 14B provide the left temperature detected signal produced from the left thermopile 13. The micro-flow sensor 1 further includes resistors 15, 16 used for acquiring the temperatures of the fluid and output terminals 17A, 17B for providing the fluid temperature signals produced from the resistors 15, 16. The right thermopile 11 and the left thermopile 13 constitute a temperature sensor.

The upstream thermopile 8, downstream thermopile 5, right thermopile 11 and left thermopile 13 are constituted by a thermocouple, respectively. The thermocouple is made of p++ —Si and Al and has a cold contact and hot contact. The thermocouple detects heat to produce a temperature detected signal on the basis of the thermal electromotive force resulting from the temperature difference between the cold contact and the hot contact.

Figure 2:
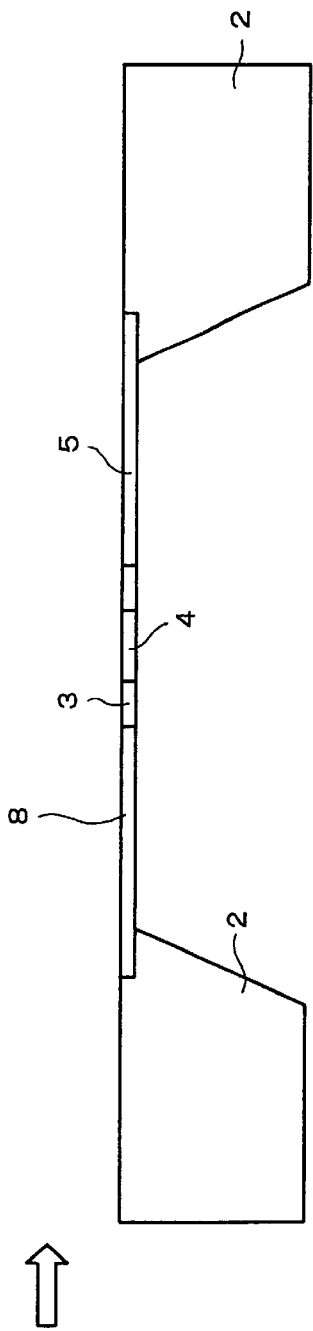
FIG. 2 is a sectional view according to the micro-flow sensor according to the first embodiment of this invention.

As seen from FIG. 2, the Si board 2 includes the diaphragm 2 on which the hot contact of each of the micro-heater 4, upstream thermopile 8, downstream thermopile 5, right thermopile 11 and left thermopile 13 is formed.

In the micro-flow sensor 1 thus configured, when the micro-heater 4 starts heating by the driving current externally supplied, the heat generated from the micro-heater 4 is conducted to the hot contact of each of the downstream thermopile 5 and the upstream thermopile 8 through the fluid. The cold contact of each of these thermopiles, which is located on the Si board 2, exhibits the temperature of the board. The hot contact of each of these thermopiles, which is located on the diaphragm, is heated by the conducted heat. The hot contact has a temperature higher than that of the board 2. Each thermopile generates a thermal electromotive force based on the temperature difference between the hot contact and cold contact to produce a temperature detected signal.

The heat conducted through the fluid is conducted to the respective thermopiles by the mutual effect of the thermal expansion of the fluid and the velocity of the fluid flowing from P to Q. More specifically, where there is no flow velocity, the heat is equally conducted to the upstream thermopile 8 and the downstream thermopile 5 by thermal expansion. Thus, the difference signal between the first temperature detected signal from the upstream thermopile 8 and the second temperature detected signal from the downstream thermopile 5 is zero.

On the other hand, when the velocity is generated in the fluid, because of the flow velocity, the quantity of heat conducted to the hot contact of the downstream thermopile 5 is increased. Thus, the difference signal between the second temperature detected signal and the first temperature detected signal is a positive value corresponding to the difference signal.

Further, when the micro-heater 4 starts heating by the driving current externally supplied, the heat generated from the micro-heater 4 is conducted to the right thermopile 11 arranged in a direction orthogonal to the flow direction of the fluid with respect to the micro-heater 4 by only the thermal expansion without being affected by the flow velocity of the fluid. Likewise, the heat generated from the micro-heater 4 is conducted to the left thermopile 13 arranged in a direction orthogonal to the flow direction of the fluid with respect to the micro-heater 4. The property of the fluid such as the thermal dispersion coefficient which is determined by thermal conduction, thermal dispersion, specific heat, etc. can be computed on the basis of the right temperature detected signal produced from the third output terminals 12A, 12B by the electromotive force of the right thermopile 11 and/or the left temperature detected signal produced from the fourth output terminals 14A, 14B by the electromotive force of the left thermopile 13.

In the micro-flow sensor 1 according to this embodiment, the micro-heater 4, upstream thermopile 8, downstream thermopile 5, right thermopile 11 and left thermopile 13 are located on the diaphragm 3. Therefore, by reducing the thermal capacity of each of these elements, power consumption can be reduced. The micro-flow sensor 1, which is simple in structure, can be manufactured at low cost.

Next, an explanation will be given of a flow rate measuring apparatus using the above micro-flow sensor which can accurately measure the flow rate of fluid at all times regardless with a change in the kind or composition of the fluid.

Figure 3:
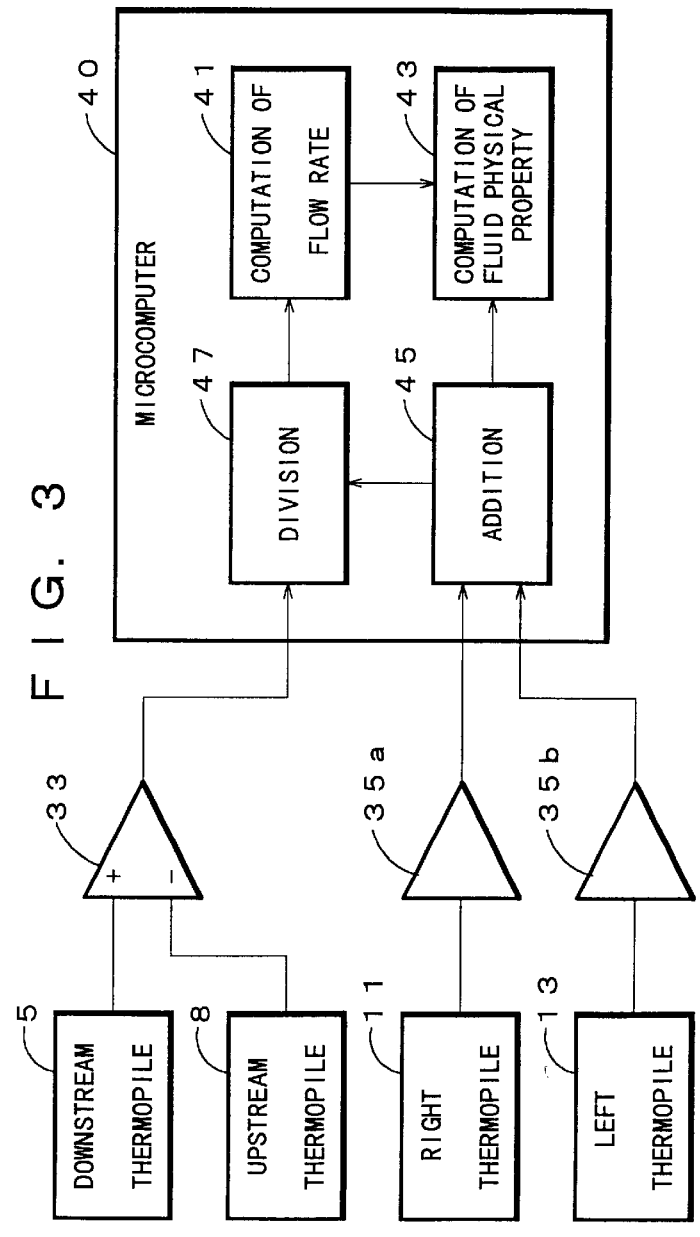
FIG. 3 is a block diagram of the arrangement of a flow rate measuring apparatus using the micro-flow sensor according to the first embodiment of this invention.

FIG. 3 is a block diagram of the arrangement of a flow rate measuring apparatus using the micro-flow sensor according to the first embodiment of this invention. The flow rate measuring apparatus intends to measure the flow rate of the fluid such as gas. The flow rate measuring apparatus includes a differential amplifier 33 for amplifying the difference signal between the second temperature detected signal (from the downstream thermopile 5 within the micro-flow sensor 1) and the first temperature detected signal (from the upstream thermopile 8 within the micro-flow sensor 1), an amplifier 35*a* for amplifying the right temperature detected signal from the right thermopile 11 within the micro-flow sensor 1, an amplifier 35*b* for amplifying the left temperature detected signal from the left thermopile 11 within the micro-flow sensor 1 and a microcomputer 40.

The microcomputer 40 includes an adder unit 45 for adding the right temperature detected signal produced from the amplifier 35*a* and the left temperature detected signal produced from the amplifier 35*b*, a divider unit for dividing the difference signal between the second temperature detected signal and the first temperature detected signal acquired by the differential amplifier 33 by an addition signal produced from the adder 45, a flow rate computing unit 41 for computing the flow rate of a fluid on the basis of an addition signal produced from the divider unit 47, and a fluid property computing unit 43 for computing the property such as the thermal conducting rate, specific heat, viscosity, density on the basis of the addition signal from the adder unit 45.

Figure 4:
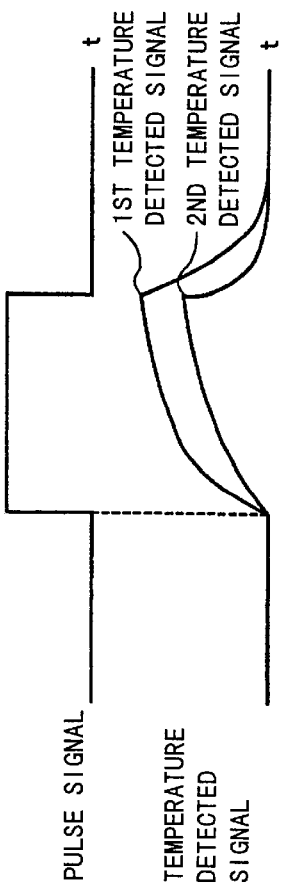
FIG. 4 is a flowchart for explaining the flow rate measuring method which is realized by the flow rate measuring apparatus shown in FIG. 3.

Referring to the flowchart shown in FIG. 4, an explanation will be given of a method of measuring a flow rate realized by the flow rate measuring apparatus related to the first embodiment.

Figure 5:
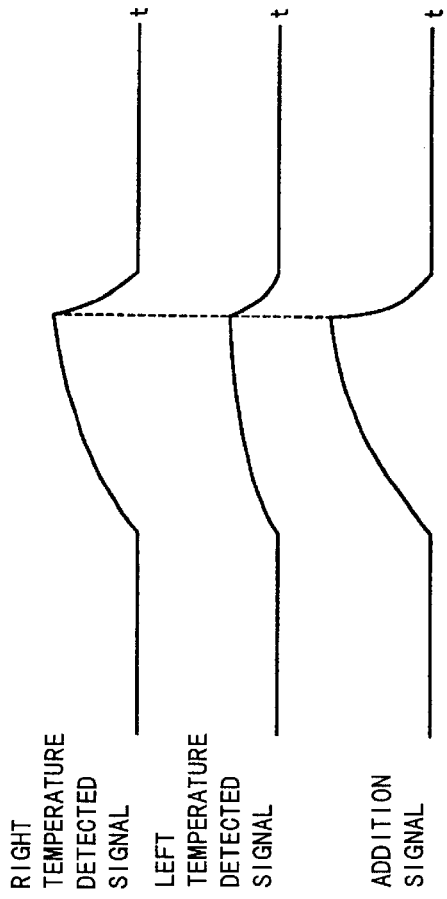
FIG. 5 is a graph showing a first temperature detected signal and a second temperature detected signal which are produced by the micro-flow sensor shown in FIG. 1.

First, when the micro-heater 4 is driven by the driving current of a pulse signal externally supplied (step S11), the second temperature detected signal is produced from the downstream thermopile 5, whereas the first temperature detected signal is produced from the upstream thermopile 8 (step S13). Both second and first temperature detected signals are supplied to the differential amplifier 33. Incidentally, FIG. 5 shows the response of the first and second temperature detected signals to the pulse signal.

Next, the differential amplifier 33 amplifies the second temperature detected signal from the downstream thermopile 5 and the first temperature detected signal from the upstream thermopile 8 (step S15).

Figure 6:
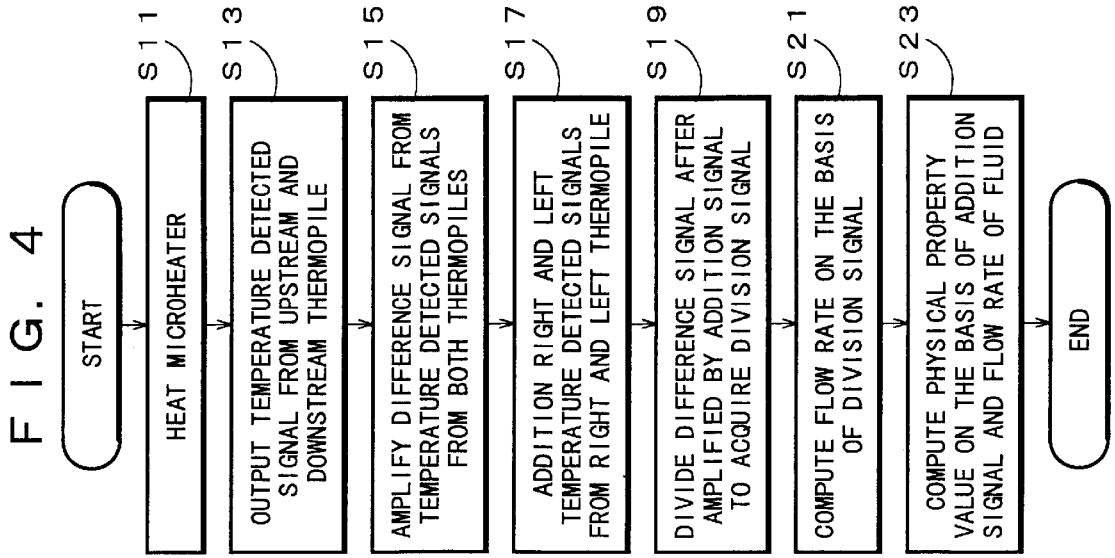
FIG. 6 is a graph showing a right temperature detected signal and a left temperature detected signal.

The adder unit 45 adds the right temperature detected signal supplied from the amplifier 35*a* and the left temperature detected signal supplied from the amplifier 35*b* to acquire an addition signal (step S17). FIG. 6 shows a timing chart of the right temperature detected signal, left temperature detected signal and addition signal. The divider unit 47 divides the difference signal after having amplified in step S15 by the addition signal acquired in step S17 to acquire a division signal (step S19).

The flow rate computing unit 41 computes the precise flow rate of the fluid on the basis of the division signal acquired in step S19 (step S21). The fluid property computing unit 43 computes the property such as the thermal conducting rate, specific heat, viscosity, density of the fluid on the basis of the addition signal acquired in step S17 and the precise flow rate computed in step S21 (step S23).

In this way, by detecting the property by the right thermopile 11 and the left thermopile 13 which are arranged in a direction orthogonal to the flow direction of the fluid, the thermal conductivity of the fluid is measured. Where the flow velocity is zero, the velocity of conducting heat through the fluid depends on the thermal diffusion coefficient (one of the properties of the fluid) which is determined by the thermal conducting coefficient, thermal diffusion and specific heat, etc. Where the flow velocity is zero, the thermal diffusion coefficient is acquired on the basis of the temperature difference between the left thermopile 13 or the right thermopile 14 and the micro-heater 4. The larger the temperature difference is, the smaller the thermal diffusion coefficient is.

The value of the thermal diffusion coefficient affects the first temperature detected signal supplied from the upstream thermopile 8 and the second temperature detected signal supplied from the downstream thermopile 5. Namely, the values of these signals vary according to the thermal diffusion coefficient. Therefore, by dividing the first temperature detected signal, second temperature detected signal or the difference therebetween by the thermal diffusion coefficient, the precise flow rate can be computed for the fluids having different thermal diffusion coefficients, i.e. any kind of fluid.

On the other hand, where the flow rate is not zero, heat is conducted downstream according to the flow of the fluid.

Therefore, the quantity of heat which reaches the right thermopile 11 and the left thermopile 13 is reduced correspondingly. Namely, the thermal diffusion around the right thermopile 11 and the left thermopile 13 is increased according to the flow of the fluid. Now, since it is known that the rate of increasing the thermal diffusion is proportional to the square root of the flow velocity of the fluid, the thermal diffusion coefficient of the fluid can be theoretically estimated for any flow rate as long as the flow rate of the fluid can be acquired by any means.

On the other hand, also around the upstream thermopile 8 and the downstream thermopile 5, an increase in the thermal diffusion (reduction of the quantity of heat moving from the micro-heater 4) is generated like around the right thermopile 11 and the left thermopile 13. Therefore, when the quantity of heat of the fluid is increased, because of the attendant increase in the thermal diffusion, the difference between the temperature of the fluid around the downstream thermopile 5 and that around the upstream thermopile 8 is decreased.

Therefore, the difference signal between the second temperature detected signal (from the downstream thermopile 5) and the first temperature detected signal (from the upstream thermopile 8), which is to be essentially increased in proportion to an increase in the flow velocity of the fluid, is decreased under the influence of the thermal diffusion. Where the flow rate of the fluid is excessively increased, the increment due to the increase in the flow velocity exceeds the decrement due to the increase in the thermal diffusion, the difference signal between the second temperature detected signal and the first temperature detected signal may be decreased although the flow rate has been increased.

In order to obviate such inconvenience, under the assumption that the addition value of the right temperature detected signal and the left temperature detected signal when the flow rate is zero is "1", the ratio of the right temperature detected signal or the left temperature detected signal when the flow rate is not zero to the addition value is regarded as a coefficient representative of the changing rate of the quantity of moving heat. This coefficient is multiplied by the difference signal between the second temperature detected signal and the first temperature detected signal.

Namely, by dividing the difference signal between the second temperature detected signal and the first temperature detected signal by the addition value of the right temperature detected signal and the left temperature detected signal, the flow rate free from the influence of a change in the thermal diffusion can be computed, thereby acquiring the precise flow rate with high resolution.

In the embodiment described above, the difference signal between the first temperature detected signal and the second temperature detected signal after having been amplified, acquired by the differential amplifier 33 is divided by the addition signal between the right temperature detected signal and the left temperature detected signal, acquired by the adder unit 45, so that the flow rate free from the influence by the thermal diffusion can be computed.

In the embodiment, the division signal is acquired by the divider unit 47 earlier than the flow rate is acquired by the flow rate computing unit. This is because it is not necessary to take the property of the fluid as the precise value such as the thermal expansion coefficient, specific heat, viscosity and density in order to exclude the influence of the thermal diffusion on the difference signal between the second temperature detected signal and the first temperature detected signal after having been amplified.

Specifically, in the embodiment described above, in order to compute the thermal expansion coefficient, specific heat, viscosity and density of the fluid, which cannot be defined unless the state of the thermal diffusion is not accurately known, by the fluid property computing unit 43, the accurate flow rate free from the influence by a change in the thermal diffusion is computed beforehand. The flow rate thus computed is reflected in the computation of the property of the fluid by the fluid property computing unit 43.

However, according to the kind of the property to be computed by the fluid property computing unit 43, the property of the fluid may be computed previously by the fluid property computing unit 43. Thereafter, the accurate flow rate free from the influence of a change in the thermal diffusion may be computed on the basis of the property thus computed and the amplified difference signal between the second temperature detected signal from the downstream thermopile 5 and the first temperature detected signal from the upstream thermopile 8.

Thus, in accordance with the flow rate measuring apparatus using the micro-flow sensor related to the first embodiment, the right thermopile 11 and the left thermopile 13 are arranged in a direction orthogonal to the flow direction of the fluid with respect to the micro-heater 4 to produce the right temperature detected signal and the left temperature detected signal. Because of such a configuration, the property of the fluid such as the thermal diffusion coefficient can be computed accurately without being affected by the flow direction of the fluid on the basis of the right temperature detected signal and the left temperature detected signal.

Further, since the flow rate of the fluid computed by the flow rate computing unit 41 is corrected on the basis of the property thus computed, the flow rate can be measured accurately with no special contrivance even when the kind and composition of the fluid is changed.

By using the new output when the output from the micro-flow sensor 1 is divided by the output from the right thermopile 11 and/or the left thermopile 13, the characteristic of the flow rate and the output can be more simply made independent from the minute change in the composition of e.g. a fuel gas.

Concrete configuration of micro-flow sensor according to the second embodiment of this invention.

Figure 7:
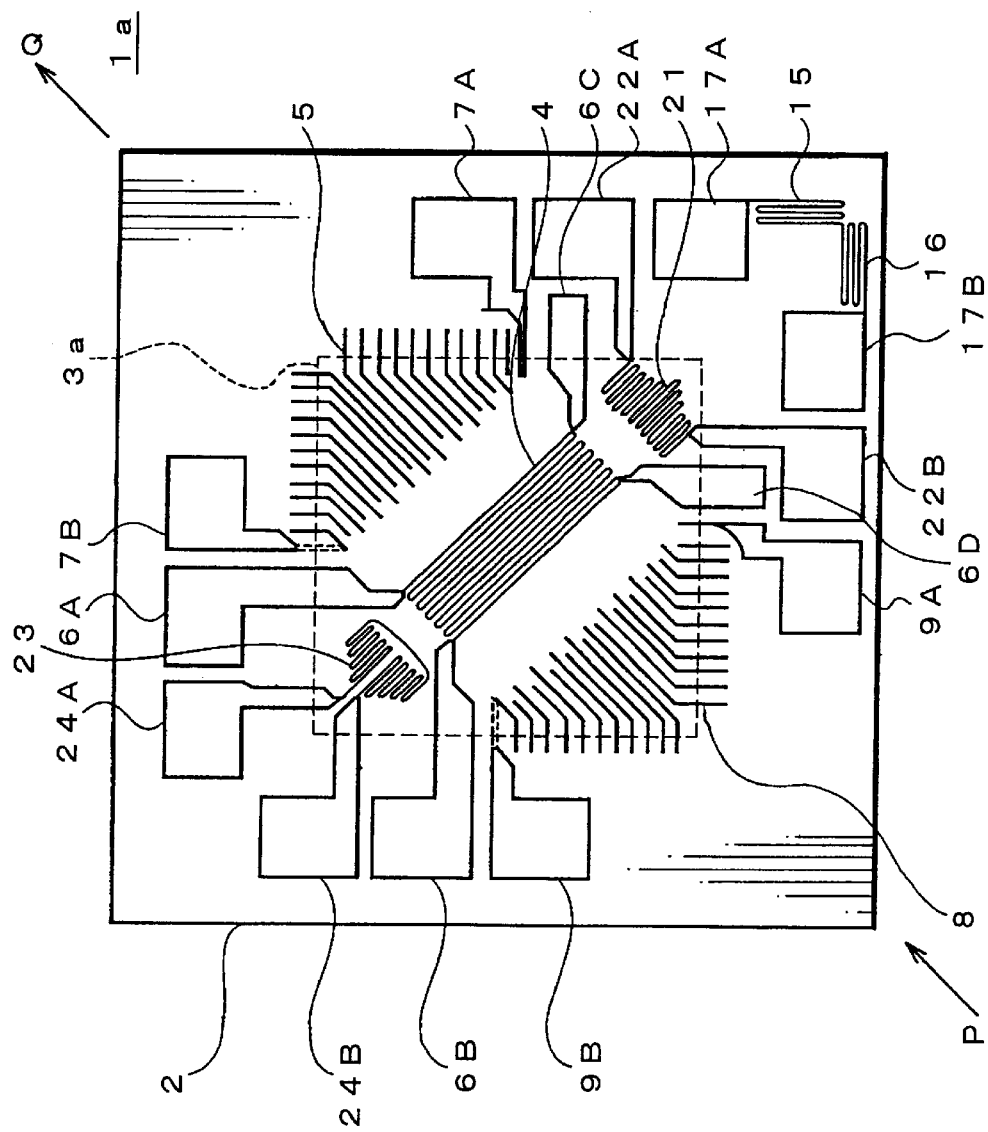
FIG. 7 is a view showing a configuration of the micro-flow sensor according to a second embodiment of this invention.
Figure 8:
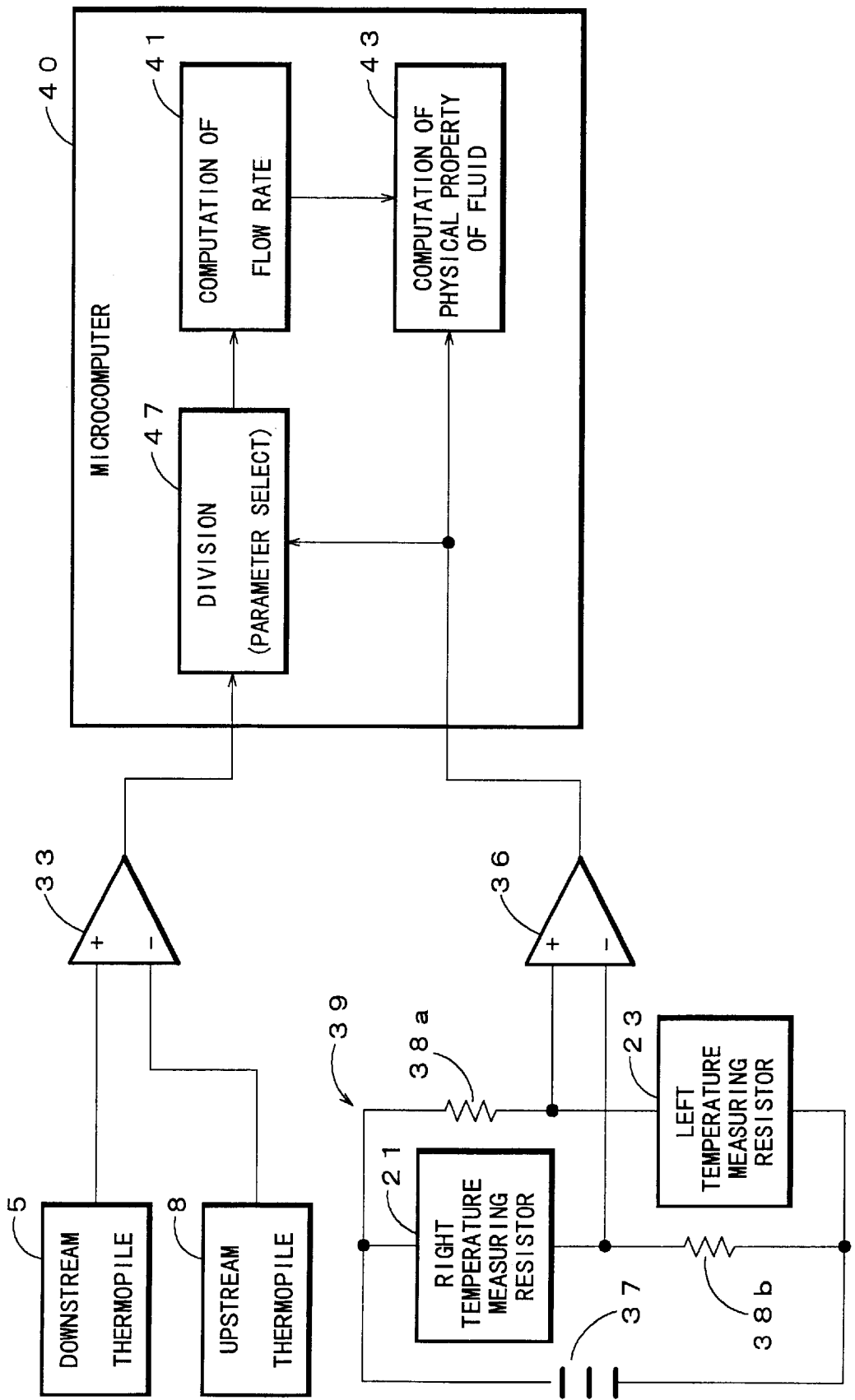
FIG. 8 is a block diagram of the arrangement of a flow rate measuring apparatus using the micro-flow sensor according to the second embodiment of this invention.
Figure 9:
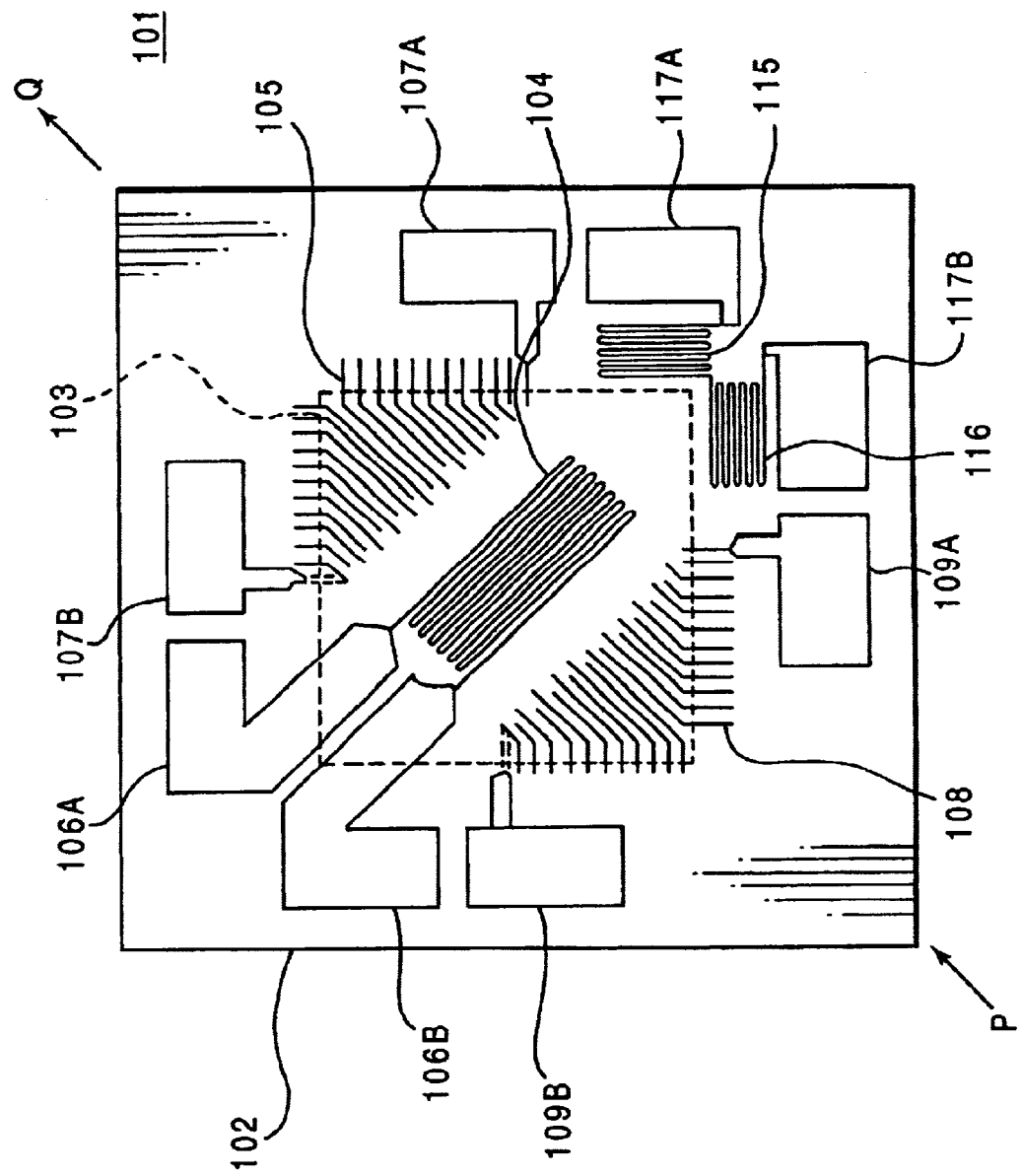
FIG. 9 is a view showing the configuration of a conventional thermal micro-flow sensor.

Referring to FIGS. 7 and 8, an explanation will be given of the configuration of the micro-flow sensor according to the second embodiment of this invention.

As seen from FIG. 7, a micro-flow sensor, generally 1a, includes a Si board 2, a diaphragm 3, a micro-heater 4, a downstream thermopile 5, power source terminals 6A, 6B, first output terminals 7A, 7B, upstream thermopile 8 and second output terminals 9A, 9B.

The micro-flow sensor 1a further includes a right temperature measuring resistor 21, third output terminals 12A, 12B, a left temperature measuring resistor 23 and fourth output terminals 14A, 14B. The right temperature measuring resistor 21 is arranged in a direction orthogonal to the flow direction (direction from P to Q) of fluid with respect to the micro-heater 4 and serves to detect the temperature of the fluid to produce a right temperature detected signal. The third output terminals 22A, 22B provide the right temperature detected signal produced from the right temperature measuring resistor 21. The left temperature measuring resistor 23 is arranged in a direction orthogonal to the flow direction of fluid with respect to the micro-heater 4 and serves to detect the temperature of the fluid to produce a left temperature detected signal. The fourth output terminals 24A, 24B provide the left temperature detected signal produced from the left temperature measuring resistor 23. The micro-flow sensor 1 further includes resistors 15, 16 and output terminals 17A, 17B. The right temperature measuring resistor 21 and the left temperature measuring resistor 23 constitute a temperature sensor, and are made of Pt and others like the micro-heater 4.

In this way, in place of the right thermopile 11 and left thermopile 13 of the micro-flow sensor 1 according to the first embodiment, in the micro-flow sensor 1a according to the second embodiment, the right temperature measuring resistor 21 and left temperature measuring resistor 23 are arranged. The right temperature measuring resistor 21 detects the temperature of the fluid to supply the right temperature detected signal to the third output terminals 22A, 22B. The left temperature measuring resistor 23 detects the temperature of the fluid to the left temperature signal to supply the fourth output terminals 24A, 24B.

The property of the fluid such as the thermal dispersion coefficient which is determined by thermal conduction, thermal dispersion, specific heat, etc. can be computed on the basis of the right temperature detected signal and the left temperature detected signal.

The flow rate measuring apparatus 1a for measuring the flow rate using the micro-flow sensor, as seen from FIG. 8, includes a differential amplifier 33 for amplifying the difference signal between the second temperature detected signal (from the downstream thermopile 5 within the micro-flow sensor 1) and the first temperature detected signal (from the upstream thermopile 8 within the micro-flow sensor 1), and a bridge circuit 39 in which the right temperature measuring resistor 21 and left temperature measuring resistor 23 are opposite to two fixed resistors 38a and 38b having equal resistances and these resistors are bridge-connected.

The flow rate measuring apparatus further includes a constant voltage source 37 for applying a constant voltage between the junction point of the right temperature measuring resistor 21 and fixed resistor 38b and the junction point of the left temperature measuring resistor 23 and the fixed resistor 38a; a differential amplifier 36 for differentially amplifying the potential between the junction point A of the right temperature measuring resistor 21 and the fixed resistor 38a and the junction point B of the left temperature measuring resistor 23 and the fixed resistor 38b; and a microcomputer 40. The microcomputer 40 includes a divider unit (or parameter selecting unit) 49, a flow rate computing unit 41 and a fluid property computing unit 43.

In the flow rate measuring apparatus using the micro-flow sensor according to the second embodiment, when the temperature of the right temperature measuring resistor 21 rises, the potential of the junction point A between the right temperature measuring resistor 21 and the fixed resistor 38a is boosted. When the temperature of the left temperature measuring resistor 23 rises, the potential of the junction point B between the left temperature measuring resistor 23 and the fixed resistor 38b is boosted. Therefore, when the differential amplification is made by the differential amplifier 36 so that the potential at the junction point A is subtracted from the potential at the junction point B, it provides an addition signal after the addition value of the right temperature detected signal and the left temperature detected signal has been amplified.

Further, the divider unit (or parameter selecting unit) 47 divides the amplified differential signal (between the second temperature detected signal from the downstream thermopile 5 and the first temperature detected signal from the upstream thermopile 8) by the amplified addition signal supplied from the differential amplifier 36, thereby providing a division signal. The flow rate computing unit 41 computes the accurate flow rate of the fluid on the basis of the division signal. The fluid property computing unit 43 computes the property of the fluid such as thermal conductivity, specific heat, viscosity, density, etc. on the basis of the accurate flow rate computed by the flow rate computing unit 41 and the amplified addition signal supplied from the differential amplifier 36.

Thus, with no special contrivance, the flow rate of the fluid can be accurately measured irrespectively of the kind and composition of the fluid. The same effect as the flow rate measuring apparatus using the micro-flow sensor according to the first embodiment can be obtained.

The present invention should not be limited to the micro-flow sensor 1, 1a, flow rate measuring apparatus and method using them. In the micro-flow sensor 1 according to the first embodiment, the thermopile was used as a temperature sensor. In the micro-flow sensor 1a according to the second embodiment, the temperature measuring resistor of Pt resistor was used as a temperature sensor. The temperature sensor should not be limited to these elements, but may be any temperature sensor such as a corrector, thermistor, etc. which are used usually.

In the micro-flow sensor 1, 1a according to the first and the second embodiment, the thermal fluid sensor consisting of the right thermopile 11, left thermopile 13 and mciroheater 4 to detect the property of the fluid was formed integrally to the micro-flow sensor 1, 1a consisting of the downstream thermopile 5, upstream thermopile 8 and micro-heater 4 to measure the flow velocity (flow rate) of the fluid. However, this thermal fluid sensor consisting of the right thermopile 11, left thermopile 13 and mciroheater 4 may be provided separately from the micro-flow sensor 1, 1a.

In this case, the property of the fluid can be computed by the fluid property computing unit 43 of the microcomputer 40 on the basis of the right temperature detected signal produced from the third output terminals 12A, 12B by the electromotive force from the right thermopile 11 and/or the left temperature detected signal produced from the fourth output terminals 14A, 14B by the electromotive force from the left thermopile. Further, the kind of the fluid can be inferred on the basis of the property of the fluid by the microcomputer 40.

As described finally in connection with the first embodiment, where the accurate flow rate of the fluid free from the influence by a change in the thermal diffusion is computed on the basis of the property previously by the fluid property computing unit 43 and the amplified difference signal from the differential amplifier 33, the amplified differential signal from the differential amplifier 33 may be corrected using a prescribed correction coefficient corresponding to the kind of the fluid inferred by the microcomputer 40, thereby computing the flow rate.

In this case, a table on which the kinds of the fluid are linked with the correction coefficients is previously stored in an internal memory (ROM) of the microcomputer 40 or an external memory (preferably non-volatile) connected to the microcomputer 40. The amplified difference signal from the differential amplifier 33 is multiplied by the correction coefficient corresponding to the kind of the inferred fluid which is read from the internal memory or external memory, thereby realizing computation of the flow rate. This relaxes the burden in the processing of computing the flow rate.

Where the property of the fluid is computed previously by the fluid property computing unit 43 and the accurate flow rate free from the influence by a change in the thermal diffusion is thereafter computed, another table may be previously stored in an internal memory (ROM) of the microcomputer 40 or an external memory (preferably non-volatile) connected to the microcomputer 40. On the table, the properties of the fluids and the kinds thereof inferred using them are linked with flow conversion equations used to acquire the flow rate of the fluid from the amplified difference signal from the differential amplifier 33.

Still another table may be previously stored in an internal memory (ROM) of the microcomputer 40 or an external memory (preferably non-volatile) connected to the microcomputer 40. On this table, the flow rate of the fluid computed by the flow rate computing unit 41 on the basis of the second temperature detected signal and the first temperature detected signal is linked with a reference value of the corresponding third temperature detected signal from the right thermopile 11 or the left thermopile 13.

In this case, the fluid property computing unit 43 of the microcomputer 40 computes the property of the fluid on the basis of the ratio of the reference value of the third temperature detected signal, which is derived from the external memory using the flow rate computed by the flow rate computing unit 41 as an address pointer, to the third temperature detected signal actually acquired from the right thermopile 11 and the left thermopile 13.

The above property of the fluid can be computed by multiplying the above ratio of the actual third temperature detected signal and its reference value by the output from the differential amplifier 33.

In the first embodiment and the second embodiment, the temperature sensors for detecting the property of the fluid were arranged on both right and lefts of the micro-heater 4. However, the temperature sensor may be arranged on one of both right and lefts to detect the temperature of the fluid, thereby computing the property of the fluid.

Where the temperature sensors are arranged on both sides of the micro-heater 4 as in the first embodiment and second embodiment, the average value of the output signals from both temperature sensors is used to detect the property of the fluid. Where the temperature sensor is arranged on one of both sides, the output therefrom is used to detect the property of the fluid.

The division by the divider unit 47 may be selectively carried out according to the value of the output from the differential amplifier 33 which results from amplifying the difference signal between the second temperature detected signal and the first temperature detected signal.

According to the experiment performed by the inventors of this invention, in the region with a relative low flow rate, the output signal values of the second temperature detected signal and the first temperature detected signal increase in proportion to the flow rate. However, in the region with a relative high flow rate, they do not increase in proportion to the flow rate, but have a tendency of saturation.

In the region with the relative low flow rate where the output signal values increase with the flow rate, the difference signal amplified by the differential amplifier 33 may be dealt with as a flow rate signal as it is. In the region with the relative high flow rate where the output signal values do not increase with the flow rate, the divider unit 49 divides the amplified difference signal from the differential amplifier 33 by the average value of the third temperature detected signals or one of them to exclude the influence of saturation of the temperature detected signal so that the divided value is used as the flow rate signal.

In such a configuration, the amplified difference signal between the second temperature detected signal and the first temperature detected signal, which could not be used for the measurement of the flow rate in the region with the relatively high flow rate as described above, can be used for this purpose together with the average value of the third temperature detected signals from the left thermopile 11 and the right thermopile 13 or one of them. In this way, the range of measurement where the flow rate can be measured accurately can be improved by 100–1000 times as large as before. This permits various leakage states in e.g. gas meter to be detected by a single sensor.

Further, it is needless to say that within the scope not departing from the technical idea of this invention, various modifications can be implemented.

INDUSTRIAL APPLICABILITY

As understood from the first and second embodiments described above, in accordance with the thermal fluid sensor accordance with this invention, in a state supported on the supporting board, a heater heats an object fluid flowing through a flow path by a driving current externally supplied. Simultaneously, a side temperature sensor arranged in an direction orthogonal to the flow direction of the object fluid with respect to the heater detects the thermal conductivity of the object fluid so that a temperature detected signal is produced. Therefore, the property of the fluid can be computed on the basis of the temperature detected signal.

In accordance with the thermal fluid sensor according to this invention, the thermal conductivity of the object fluid is detected by two side temperature sensors are arranged on both sides of the heater in a direction orthogonal to the flow direction of the object fluid. Therefore, even when there is a change in the flow of the object fluid in the flow path in a direction orthogonal to the flow direction, the property of the fluid can be accurately computed on the basis of the temperature detected signals from both side temperature sensors.

In accordance with the thermal fluid sensor, the heater and the side temperature sensor are formed on the diaphragm. The thermal capacity of the heater and temperature sensor can be decreased to reduce power consumption.

In accordance with the thermal fluid sensor according to this invention, the side temperature sensor is a thermopile. Therefore, the temperature detected signal provides a small change in the characteristic which depends on a change in the temperature. This contributes to accurate measurement of the flow rate. Since the thermopile itself does not generate heat, correction is not required. Since the thermopile produces an output signal due to its own electromotive force, it does not consume the power.

In accordance with the thermal fluid sensor according to this invention, the side temperature sensor is a resistor. Therefore, the high response speed and sensitivity to the temperature detected signal can be provided so that the flow rate can be measured at a high speed. Since the resistor produces an output signal due to its own electromotive force, it does not consume the power.

In accordance with the fluid discriminating apparatus according to this invention, a fluid property computes the property of the object fluid on the basis of the temperature detected signal supplied from the side temperature sensor in the thermal fluid sensor. The fluid property can be used to correct the output from the flow rate sensor which varies according to the kind or composition of the object fluid, or to decide that the kind or composition of the object fluid flowing through the flow path has changed.

In accordance with the fluid discriminating apparatus according to this invention, a reference value storage means stores a plurality of kinds of reference values of the temperature detected signal supplied from the side temperature sensor within the thermal fluid sensor, the reference values corresponding to flow rates of the object fluid flowing through the flow path. The reference value inferring means infers a single reference value corresponding to the flow rate of the object fluid measured by the flow rate measuring means from the plurality of kinds of reference values stored in the reference value storage means. The temperature detected signal ratio computing means for computing a ratio of the reference value inferred by the reference value inferring means to the temperature detected signal supplied from the side temperature sensor. Therefore, the fluid property computing means can easily compute the property of the object fluid on the basis of the ratio computed by the temperature detected signal ratio computing means.

In accordance with the fluid discriminating apparatus according to this invention, the fluid property computing means multiplies the flow rate or its square root of the object fluid flowing through the flow path measured by the flow rate measuring means by the temperature detected signal supplied from the side temperature sensor in the thermal fluid sensor. In this configuration, the fluid property computing means can easily compute the property of the object fluid flowing through the flow path.

In accordance with the fluid discriminating apparatus according to this invention, the kind of the object fluid discriminated by the kind discriminating means is used to correct the output from the flow rate sensor and discriminate a change in the kind or the composition of the fluid flowing through the flow path.

In accordance with the fluid discriminating apparatus according to this invention, reference range data storage means stores data of a plurality of kinds of reference ranges of the temperature detected signal corresponding to the flow rates of the object fluid flowing through the flow path, the reference ranges being different according to the kinds of the object fluid and correlated with the kinds. The reference range data inferring means infers a single reference range data corresponding to the flow rate of the object fluid from data of the plurality of reference ranges stored in the reference range data storage means. The pertinent reference range determining means determines the reference range correlated with the object fluid to which the temperature detected signal belongs. On the basis of the reference range thus determined, the kind of the object fluid flowing through the flow path can be easily discriminated. The kind of the object fluid thus discriminated is used to correct the output from the flow rate sensor and discriminate a change in the kind or the composition of the fluid flowing through the flow path.

In accordance with the fluid discriminating method of discriminating the object fluid, in a fluid-property computing step, the property of the object fluid is computed on the basis of the temperature detected signal supplied from the side temperature sensor in the thermal fluid sensor. The property of the object fluid thus computed is used to correct the output from the flow rate sensor which varies according to the kind and composition of the object fluid and to discriminate a change in the kind or the composition of the fluid flowing through the flow path.

In accordance with the fluid discriminating method, in the fluid kind discriminating step, the kind of the object fluid is discriminated on the basis of the property of the object fluid. The kind of the fluid thus criminated can be used to correct the output from the flow rate sensor which varies according to the kind and composition of the object fluid.

In accordance with the fluid discriminating method according to this invention, in the reference value inferring step, a single reference value corresponding to the flow rate of the object fluid measured in the flow rate measuring step is inferred from a plurality of kinds of reference values of the temperature detected signal supplied from the side temperature sensor within the thermal fluid sensor, the reference values corresponding to flow rates of the object fluid flowing through the flow path. In the temperature detected signal ratio computing step, a ratio of the reference value inferred by the reference value inferring means to the temperature detected signal supplied from the side temperature sensor is computed. In the fluid property computing step, the property of the object fluid can be easily computed on the basis of the ratio thus computed.

In accordance with the fluid discriminating method according to this invention, in the fluid property computing step, the flow rate or its square root of the object fluid flowing through the flow path measured by the flow rate measuring means is multiplied by the temperature detected signal supplied from the side temperature sensor in the thermal fluid sensor, thereby easily acquiring the property of the object fluid.

In accordance with the fluid discriminating method according to this invention, in the flow rate measuring step, the flow rate of the object fluid flowing through the fluid path is measured; in the reference range data inferring step, a single reference range data corresponding to the flow rate of the object fluid is inferred from a group of data of a plurality of prescribed reference ranges of the temperature detected signal corresponding to the flow rates of the object fluid flowing through the flow path, the reference ranges being different according to the kinds of the object fluid and correlated with the kinds; in the pertinent reference range determining step, the reference range correlated with the object fluid to which the temperature detected signal belongs is determined. On the basis of the reference range thus determined, the kind of the fluid flowing through the flow path can be easily discriminated. The kind of the object fluid thus discriminated can be used to correct the output from the flow rate sensor which varies according to the kind or composition of the fluid and discriminate a change in the kind or the composition of the fluid flowing through the flow path.

In accordance with the flow rate measuring apparatus according to this invention, on the basis of the temperature detected signal from the side temperature sensor in the thermal fluid sensor, the flow rate of the fluid measured by the flow rate measuring means is corrected by the flow rate correcting means. Therefore, the flow rate of the object fluid can be measured accurately according to the kind or composition of the object fluid.

In accordance with the flow rate measuring apparatus according to this invention, the flow rate measuring means provides an output signal having a value corresponding to the measured flow rate of the object fluid flowing through the flow path, and the flow rate correcting means produces a flow rate detected signal when the output signal is divided by the temperature detected signal. Therefore, the flow rate measured by the flow rate measuring means can be easily corrected.

In accordance with the flow rate measuring apparatus according to this invention, the flow rate of the object fluid flowing through the flow path is measured; whether the flow rate of the fluid measured by the flow rate measuring means is in a high flow rate state or a low flow rate is decided; an output signal from the flow rate measuring means is produced as a flow rate detected signal as it is if the flow rate is decided to be in the low flow rate state, and another output signal when the output signal from the flow rate measuring means is divided by the temperature detected signal from the side temperature sensor is produced if the flow rate is decided to be in the high flow rate state. In this way, the flow rate of the fluid can be measured accurately in a wider range.

In accordance with the flow rate measuring apparatus according to this invention; a single parameter is selected from the plurality of kinds of parameters stored in the parameter storage means on the basis of the property of the object fluid computed by the fluid property computing means, and the flow rate converted from the output signal from the flow rate measuring means using the single parameter selected by the selecting means is taken as the measured value of the flow rate of the object fluid flowing through the flow path. Therefore, the flow rate of the fluid can be measured accurately according to the kind or composition which defines the property of the object fluid.

In accordance with the flow rate measuring method according to this invention, on the basis of the temperature detected signal from the side temperature sensor in the thermal fluid sensor, the flow rate of the fluid measured in the flow rate measuring step is corrected in the flow rate correcting step. Therefore, the flow rate of the object fluid can be measured accurately according to the kind or composition of the object fluid.

In accordance with the flow rate measuring method according to this invention, the flow rate measuring step provides an output signal having a value corresponding to the measured flow rate of the object fluid flowing through the flow path, and the flow rate correcting step produces a flow rate detected signal when the output signal is divided by the temperature detected signal. Therefore, the flow rate measured by the flow rate measuring step can be easily corrected.

In accordance with the flow rate measuring method according to this invention, the flow rate of the object fluid flowing through the flow path is measured; whether the flow rate of the fluid measured in the flow rate measuring step is in a high flow rate state or a low flow rate is decided; an output signal acquired in the flow rate measuring: step is produced as a flow rate detected signal as it is if the flow rate is decided to be in the low flow rate state, and another output signal when the output signal from the flow rate measuring step is divided by the temperature detected signal from the side temperature sensor is produced if the flow rate is decided to be in the high flow rate state. In this way, the flow rate of the fluid can be measured accurately in a wider range.

In accordance with the flow rate measuring method according to this invention; a single parameter is selected from the plurality of kinds of prescribed parameters on the basis of the property of the object fluid computed by the fluid property computing step, and the flow rate converted from the output signal from the flow rate measuring step using the single parameter selected in the selecting step is taken as the measured value of the flow rate of the object fluid flowing through the flow path. Therefore, the flow rate of the fluid can be measured accurately according to the kind or composition which defines the property of the object fluid.

In accordance with the flow sensor according to this invention, a heater supported by a supporting board heats an object fluid flowing through a flow path by a driving current externally supplied. Simultaneously, the upstream temperature sensor arranged upstream of the object fluid with respect to the heater detects the temperature of the object fluid so that a first temperature detected signal is produced. The downstream temperature sensor arranged downstream of the object fluid with respect to the heater also detects the temperature of the object fluid so that a second temperature detected signal is produced. The side temperature sensor arranged in a direction orthogonal to the flow direction of the object fluid with respect to the heater to detect the temperature of the object fluid so that a third temperature detected signal is produced. Therefore, the property of the fluid can be computed on the basis of the third temperature detected signal.

In accordance with the flow sensor according to this invention, two side temperature sensors are arranged on both sides of the heater in a direction orthogonal to the flow direction of the object fluid. Therefore, even when there is a variation in the flow of the object fluid in the flow path in a direction orthogonal to the flow direction, the property of the fluid can be accurately computed on the basis of the third temperature detected signals from both side temperature sensors.

In accordance with the flow sensor according to this invention, the heater, the upstream temperature sensor, the downstream temperature sensor and the side temperature sensor are formed on the diaphragm. The thermal capacity of the heater and temperature sensors can be decreased to reduce power consumption.

In accordance with the flow sensor according to this invention, the upstream temperature sensor and the downstream temperature sensors are a thermopile, respectively. Therefore, the difference signal between the first and the second temperature detected signal provides a small change in the characteristic which depends on a change in the temperature. This contributes to accurate measurement of the flow rate. Since the thermopile itself does not generate heat, correction is not required. Since the thermopile produces an output signal due to its own electromotive force, it does not consume the power.

In accordance with the flow sensor according to this invention, the upstream sensor and the downstream sensors are a collector, respectively. Therefore, the high response speed and sensitivity to the temperature detected signal can be provide so that the flow rate can be measured at a high speed. Since the collector produces an output signal due to its own electromotive force, it does not consume the power.

In accordance with the flow sensor according to this invention, since the side temperature sensor is a thermopile, Therefore, the third temperature detected signal provides a small change in the characteristic which depends on a change in the temperature. This contributes to accurate measurement of the flow rate. Since the thermopile itself does not generate heat, correction is not required. Since the thermopile produces an output signal due to its own electromotive force, it does not consume the power.

In accordance with the flow sensor according to this invention, the side temperature sensor is a collector, respectively. Therefore, the high response speed and sensitivity to the third temperature detected signal can be provide so that the flow rate can be measured at a high speed. Since the collector produces an output signal due to its own electromotive force, it does not consume the power.

In accordance with the fluid discriminating apparatus according to this invention, the flow rate measuring means measures a flow rate of the object fluid on the basis of a difference signal between the first temperature detected signal supplied from the upstream temperature sensor and the second temperature detected signal supplied from the downstream temperature sensor; reference value storage means stores a plurality of kinds of reference values of the third temperature detected signal supplied from the side temperature sensor within the flow sensor, the reference values corresponding to flow rates of the object fluid flowing through the flow path; reference value inferring means infers a single reference value corresponding to the flow rate of the object fluid measured by the flow rate measuring means from the plurality of kinds of reference values stored in the reference value storage means; and temperature detected signal ratio computing means for computing a ratio of the reference value inferred by the reference value inferring means to the third temperature detected signal supplied from the side temperature sensor. Thus, the fluid property computing means can easily compute the property of the object fluid on the basis of the ratio computed by the temperature detected signal ratio computing means. The property of the object fluid thus discriminated can be used to correct the output from the flow rate sensor which varies according to the kind or composition of the fluid and discriminate a change in the kind or the composition of the fluid flowing through the flow path.

In accordance with the fluid discriminating apparatus according to this invention, flow rate measuring means measures a flow rate of the object fluid on the basis of a difference signal between the first temperature detected signal supplied from the upstream temperature sensor and the second temperature detected signal supplied from the downstream temperature sensor; and fluid property computing means multiplies the flow rate or its square root of the object fluid flowing through the flow path measured by the flow rate measuring means by the third temperature detected signal supplied from the side temperature sensor in the flow sensor, thereby acquiring the property of the object fluid. The property of the object fluid thus computed can be used to correct the output from the flow rate sensor which varies according to the kind or composition of the fluid and discriminate a change in the kind or the composition of the fluid flowing through the flow path.

In accordance with the fluid discriminating apparatus according to this invention, fluid kind discriminating means discriminates the kind of the object fluid on the basis of the property of the object fluid. The kind of the object fluid thus discriminated can be used to correct the output from the flow rate sensor which varies according to the kind or composition of the fluid.

In accordance with the fluid discriminating apparatus according to this invention, the flow rate measuring means measures a flow rate of the object fluid on the basis of a difference signal between the first temperature detected signal supplied from the upstream temperature sensor and the second temperature detected signal supplied from the downstream temperature sensor; and reference range data inferring means infers a single reference range data corresponding to the flow rate of the object fluid from data of the plurality of reference ranges of the third temperature detected signal corresponding to flow rates of the object fluid flowing through the flow path, the reference ranges being different according to the kinds of the object fluid and correlated with the kinds; and the pertinent reference range determining means determines the reference range correlated with the object fluid to which the third temperature detected signal belongs. In this case, the kind of the object fluid can be easily discriminated on the basis of the reference range thus determined. The kind of the object fluid thus discriminated can be used to correct the output from the flow rate sensor which varies according to the kind or composition of the fluid and discriminate a change in the kind or the composition of the fluid flowing through the flow path.

In accordance with the fluid discriminating method, in the flow rate measuring step, a flow rate of the object fluid is measured on the basis of a difference signal between the first temperature detected signal supplied from the upstream temperature sensor and the second temperature detected signal supplied from the downstream temperature sensor; in the reference value storage step, a plurality of kinds of reference values of the third temperature detected signal supplied from the side temperature sensor within the flow sensor are stored, the reference values corresponding to flow rates of the object fluid flowing through the flow path; in the reference value inferring step, a single reference value corresponding to the flow rate of the object fluid measured by the flow rate measuring means is inferred from the plurality of kinds of reference values stored in the reference value storage means; and in the temperature detected signal ratio computing step, a ratio of the reference value inferred in the reference value inferring step to the third temperature detected signal supplied from the side temperature sensor is computed; and in the fluid property computing step, the property of the object fluid is computed on the basis of the ratio thus computed. In this case, the property of the object fluid thus computed can be used to correct the output from the flow rate sensor which varies according to the kind or composition of the fluid and discriminate a change in the kind or the composition of the fluid flowing through the flow path.

In accordance with the fluid discriminating method according to this invention, in the flow rate measuring step, a flow rate of the object fluid is computed on the basis of a difference signal between the first temperature detected signal supplied from the upstream temperature sensor and the second temperature detected signal supplied from the downstream temperature sensor; and in the fluid property computing step, the flow rate or its square root of the object fluid flowing through the flow path measured by the flow rate measuring means is multiplied by the temperature detected signal supplied from the side temperature sensor in the flow sensor, thereby acquiring the property of the object fluid. In this case, the property of the object fluid thus acquired can be used to correct the output from the flow rate sensor which varies according to the kind or composition of the fluid and discriminate a change in the kind or the composition of the fluid flowing through the flow path.

In accordance with the fluid discriminating method, in the fluid kind discriminating step, the kind of the object fluid is discriminated on the basis of the property of the object fluid. The kind of the object fluid thus computed can be used to correct the output from the flow rate sensor which varies according to the kind or composition of the object fluid.

In accordance with the fluid discriminating method according to this invention, in the flow rate measuring step, a flow rate of the object fluid is measured on the basis of a difference signal between the first temperature detected signal supplied from the upstream temperature sensor and the second temperature detected signal supplied from the downstream temperature sensor; and in the reference range data inferring step, a single reference range data corresponding to the flow rate of the object fluid is inferred from data of a plurality kinds of reference ranges the third temperature detected signal corresponding flow rates of the object fluid flowing through the flow path, the reference ranges being different according to the kinds of the object fluid and correlated with the kinds; and in the pertinent reference range determining step, the reference range correlated with the object fluid to which the third temperature detected signal belongs is determined. In this case, the kind of the object fluid can be easily discriminated on the basis of the reference range thus determined. The kind of the object fluid thus discriminated can be used to correct the output from the flow rate sensor which varies according to the kind or composition of the fluid and discriminate a change in the kind or the composition of the fluid flowing through the flow path.

In accordance with the flow rate measuring apparatus, the flow rate computing means computes a flow rate of the object fluid on the basis of a difference signal between the first temperature detected signal supplied from the upstream temperature sensor and the second temperature detected signal supplied from the downstream temperature sensor; and the fluid property computing means computes the property of the object fluid on the basis of the third temperature detected signal supplied from the side temperature sensor with the flow sensor; and flow rate correcting means corrects the flow rate of the object fluid computed by the flow rate computing means on the basis of the property of the object fluid computed by the fluid property computing means. This permits the flow rate to be measured accurately even when the kind or composition of the fluid is changed.

In accordance with the flow rate measuring apparatus according to this invention, the flow rate correcting means produces a flow rate detected signal when the difference signal is divided by the third temperature detected signal. This permits the flow rate measured by the flow rate measuring means to be easily corrected.

In accordance with the flow rate measuring apparatus, the flow rate computing means computes a flow rate of the object fluid on the basis of a difference signal between the first temperature detected signal supplied from the upstream temperature sensor and the second temperature detected signal supplied from the downstream temperature sensor; and deciding means decides whether the flow rate of the fluid measured by the flow rate measuring means is in a high flow rate state or a low flow rate; and flow rate outputting means outputs an output signal from the flow rate measuring means as a flow rate detected signal as it is if the flow rate is decided to be in the low flow rate state, and another output signal when the output signal from the flow rate measuring means is divided by the third temperature detected signal from the side temperature sensor if the flow rate is decided to be in the high flow rate state. In this way, the flow rate of the fluid can be measured accurately in a wider range.

In accordance with the flow rate measuring apparatus according to this invention, a single parameter is selected from the plurality of kinds of parameters stored in the parameter storage means on the basis of the property of the object fluid computed by the fluid property computing means, and the flow rate converted from the output signal from the flow rate computing means using the single parameter selected by the selecting means is taken as the measured value of the flow rate of the object fluid flowing through the flow path. Therefore, the flow rate of the fluid can be measured accurately according to the kind or composition which defines the property of the object fluid.

In accordance with the flow rate measuring method, in the flow rate computing step, a flow rate of the object fluid is computed on the basis of a difference signal between the first temperature detected signal supplied from the upstream temperature sensor and the second temperature detected signal supplied from the downstream temperature sensor; and in the fluid property computing step, the property of the object fluid is computed on the basis of the third temperature detected signal supplied from the side temperature sensor with the flow sensor; and in the flow rate correcting step, the flow rate of the object fluid computed in the flow rate computing step is corrected on the basis of the property of the object fluid computed in the fluid property computing step. This permits the flow rate to be measured accurately even when the kind or composition of the fluid is changed.

In accordance with the flow rate measuring method according to this invention, in the flow rate correcting step, a flow rate detected signal when the difference signal is divided by the third temperature detected signal is produced. This permits the flow rate measured by the flow rate measuring step to be easily corrected.

In accordance with the flow rate measuring method, in the flow rate computing step, the flow rate of the object fluid is computed on the basis of a difference signal between the first temperature detected signal supplied from the upstream temperature sensor and the second temperature detected signal supplied from the downstream temperature sensor; and in the deciding step, it is decided whether the flow rate of the fluid measured in the flow rate measuring step is in a high flow rate state or a low flow rate; and in the flow rate outputting step, outputted are an output signal acquired in the flow rate measuring step as a flow rate detected signal as it is if the flow rate is decided to be in the low flow rate state, and another output signal when the output signal from the flow rate measuring step is divided by the third temperature detected signal from the side temperature sensor if the flow rate is decided to be in the high flow rate state. In this way, the flow rate of the fluid can be measured accurately in a wider range.

In accordance with the flow rate measuring method according to this invention, a single parameter is selected from the plurality of kinds of parameters stored in the parameter storage step on the basis of the property of the object fluid computed by the fluid property computing step, and the flow rate converted from the output signal from the flow rate computing step using the single parameter selected by the selecting step is taken as the measured value of the flow rate of the object fluid flowing through the flow path. Therefore, the flow rate of the fluid can be measured accurately according to the kind or composition which defines the property of the object fluid.

What is claimed is:
1. A thermal fluid sensor comprising:
   a heater for heating an object fluid for measurement flowing through a flow path by a driving current externally supplied;
   a side temperature sensor arranged in a direction orthogonal to the flow direction of the object fluid with respect to the heater and located on a side of the heater not upstream and not downstream of the object fluid with respect to the heater, to detect the temperature of the object fluid so that a temperature detected signal is produced;
   a supporting board for supporting the heater and the side temperature sensor; and
   flow rate measuring means for measuring a flow rate of the object fluid flowing through the flow path.
2. A thermal fluid sensor according to claim 1, wherein two side temperature sensors are arranged on both sides of the heater in a direction orthogonal to the flow direction of the object fluid.
3. A thermal fluid sensor according to claim 1, wherein the supporting board has a diaphragm whose periphery is fixed, and the heater and the side temperature sensor are formed on the diaphragm.

4. A thermal fluid sensor according to claim 1, wherein the side temperature sensor is a thermopile.

5. A thermal fluid sensor according to claim 1, wherein the side temperature sensor is a resistor.

6. A fluid discriminating apparatus for discriminating the kind of the object fluid using the thermal fluid sensor set forth in claim 1, comprising:
fluid property computing means for computing the property of the object fluid on the basis of the temperature detected signal supplied from the side temperature sensor in the thermal fluid sensor.

7. A fluid discriminating apparatus according to claim 6, comprising:
reference value storage means for storing a plurality of kinds of reference values of the temperature detected signal supplied from the side temperature sensor within the thermal fluid sensor, the reference values corresponding to flow rates of the object fluid flowing through the flow path;
reference value inferring means for inferring a single reference value corresponding to the flow rate of the object fluid measured by the flow rate measuring means from the plurality of kinds of reference values stored in the reference value storage means; and
temperature detected signal ratio computing means for computing a ratio of the reference value inferred by the reference value inferring means to the temperature detected signal supplied from the side temperature sensor,
wherein the fluid property computing means computes the property of the object fluid on the basis of the ratio computed by the temperature detected signal ratio computing means.

8. A fluid discriminating apparatus according to claim 6, wherein the fluid property computing means multiplies the flow rate or its square root of the object fluid flowing through the flow path measured by the flow rate measuring means by the temperature detected signal supplied from the side temperature sensor in the thermal fluid sensor, thereby acquiring the property of the object fluid.

9. A fluid discriminating apparatus according to claim 6, further comprising: fluid kind discriminating means for discriminating the kind of the object fluid on the basis of the property of the object fluid.

10. A fluid discriminating apparatus for discriminating the kind of the object fluid using the thermal fluid sensor set forth in claim 1, comprising:
flow rate measuring means for measuring the flow rate of the object fluid flowing through the fluid path;
reference range data storage means for storing data of a plurality of kinds of reference ranges of the temperature detected signal corresponding to the flow rates of the object fluid flowing through the flow path, the reference ranges being different according to the kinds of the object fluid and correlated with the kinds;
reference range data inferring means for inferring a single reference range data corresponding to the flow rate of the object fluid from data of the plurality of reference ranges stored in the reference range data storage means;
pertinent reference range determining means for determining the reference range correlated with the object fluid to which the temperature detected signal belongs,
wherein it is determined that the object fluid correlated with the reference range thus determined is the object fluid flowing through the flow path.

11. A fluid discriminating method of discriminating the object fluid using the thermal fluid sensor set forth in claim 1, comprising:
fluid-property computing step of computing the property of the object fluid on the basis of the temperature detected signal supplied from the side temperature sensor in the thermal fluid sensor.

12. A fluid discriminating method according to claim 11, further comprising: fluid kind discriminating step of discriminating the kind of the object fluid on the basis of the property of the object fluid.

13. A fluid discriminating method according to claim 11 comprising:
flow rate measuring step of measuring a flow rate of the object fluid flowing through the flow path;
reference value inferring step of inferring a single reference value corresponding to the flow rate of the object fluid measured in the flow rate measuring step from a plurality of kinds of reference values of the temperature detected signal supplied from the side temperature sensor within the thermal fluid sensor, the reference values corresponding to flow rates of the object fluid flowing through the flow path; and
temperature detected signal ratio computing step of computing a ratio of the reference value inferred by the reference value inferring means to the temperature detected signal supplied from the side temperature sensor,
wherein the fluid property computing step computes the property of the object fluid on the basis of the ratio computed in the temperature detected signal ratio computing step.

14. A fluid discriminating method according to claim 11, wherein the fluid property computing step multiplies the flow rate or its square root of the object fluid flowing through the flow path measured by the flow rate measuring means by the temperature detected signal supplied from the side temperature sensor in the thermal fluid sensor, thereby acquiring the property of the object fluid.

15. A fluid discriminating method for discriminating the kind of the object fluid using the thermal fluid sensor set forth in claim 1, comprising:
flow rate measuring step of measuring the flow rate of the object fluid flowing through the fluid path;
reference range data inferring step of inferring a single reference range data corresponding to the flow rate of the object fluid from a group of data of a plurality of prescribed reference ranges of the temperature detected signal corresponding to the flow rates of the object fluid flowing through the flow path, the reference ranges being different according to the kinds of the object fluid and correlated with the kinds;
pertinent reference range determining step of determining the reference range correlated with the object fluid to which the temperature detected signal belongs,
wherein it is determined that the object fluid correlated with the reference range thus determined is the object fluid flowing through the flow path.

16. A flow rate measuring apparatus for measuring the flow rate of the object fluid flowing through the flow path using the thermal fluid sensor set forth in claim 1, comprising:
flow rate measuring means for measuring the flow rate of the object fluid flowing through the flow path; and
flow rate correcting means for correcting the flow rate of the fluid measured by the flow rate measuring means.

17. A flow rate measuring apparatus according to claim 16, wherein the flow rate measuring means provides an output signal having a value corresponding to the measured flow rate of the object fluid flowing through the flow path, and the flow rate correcting means produces a flow rate detected signal when the output signal is divided by the temperature detected signal, thereby correcting the flow rate measured by the flow rate measuring means.

18. A flow rate measuring apparatus for measuring the flow rate of the object fluid flowing through the flow path using the thermal fluid sensor set forth in claim 1, comprising:
   flow rate measuring means for measuring the flow rate of the object fluid flowing through the flow path;
   deciding means for deciding whether the flow rate of the fluid measured by the flow rate measuring means is in a high flow rate state or a low flow rate;
   flow rate outputting means for outputting an output signal from the flow rate measuring means as a flow rate detected signal as it is if the flow rate is decided to be in the low flow rate state, and another output signal when the output signal from the flow rate measuring means is divided by the temperature detected signal from the side temperature sensor if the flow rate is decided to be in the high flow rate state.

19. A flow rate measuring apparatus for measuring the flow rate of the object fluid flowing through the flow path using the thermal fluid sensor set forth in claim 1,
   flow rate measuring means for measuring the flow rate of the fluid flowing through the flow path and producing an output signal having a value corresponding to the flow rate thus measured;
   fluid property computing means for computing the property of the object fluid on the basis of the temperature detected signal supplied from the side temperature sensor in the thermal fluid sensor;
   parameter storage means storing a plurality of kinds of parameters each for converting the output signal from the flow rate measuring means into a flow rate; and
   selecting means for selecting a single parameter of the plurality of kinds of parameters stored in the parameter storage means on the basis of the property of the object fluid computed by the fluid property computing means, wherein
      the flow rate converted from the output signal from the flow rate measuring means using the single parameter selected by the selecting means is taken as the measured value of the flow rate of the object fluid flowing through the flow path.

20. A flow rate measuring method for measuring the flow rate of the object fluid flowing through the flow path using the thermal fluid sensor set forth in claim 1, comprising:
   flow rate measuring step of measuring the flow rate of the object fluid flowing through the flow path; and
   flow rate correcting step of correcting the flow rate of the fluid measured by the flow rate measuring means.

21. A flow rate measuring method according to claim 20, wherein the flow rate measuring step provides an output signal having a value corresponding to the measured flow rate of the object fluid flowing through the flow path, and the flow rate correcting step produces a flow rate detected signal when the output signal is divided by the temperature detected signal, thereby correcting the flow rate measured by the flow rate measuring step.

22. A flow rate measuring method for measuring the flow rate of the object fluid flowing through the flow path using the thermal fluid sensor set forth in claim 1, comprising:
   flow rate measuring step of measuring the flow rate of the object fluid flowing through the flow path;
   deciding step of deciding whether the flow rate of the fluid measured by the flow rate measuring means is in a high flow rate state or a low flow rate;
   flow rate outputting step of outputting an output signal acquired in the flow rate measuring step as a flow rate detected signal as it is if the flow rate is decided to be in the low flow rate state, and another output signal when the output signal acquired in the flow rate measuring step is divided by the temperature detected signal from the side temperature sensor if the flow rate is decided to be in the high flow rate state.

23. A flow rate measuring method for measuring the flow rate of the object fluid flowing through the flow path using the thermal fluid sensor set forth in claim 1,
   flow rate measuring step of measuring the flow rate of the fluid flowing through the flow path and producing an output signal having a value corresponding to the flow rate thus measured;
   fluid property computing step of computing the property of the object fluid on the basis of the temperature detected signal supplied from the side temperature sensor in the thermal fluid sensor;
   selecting means for selecting a single parameter of a plurality of kinds of prescribed parameters on the basis of the property of the object fluid computed in the fluid property computing step, the plurality of kinds of parameters each for converting the output signal from the flow rate measuring means into a flow rate,
   wherein the flow rate converted from the output signal from the flow rate measuring means using the single parameter selected in the selecting step is taken as the measured value of the flow rate of the object fluid through the flow path.

24. A flow sensor comprising:
   a heater for heating an object fluid for measurement flowing through a flow path by a driving current externally supplied;
   an upstream temperature sensor arranged upstream of the object fluid with respect to the heater to detect the temperature of the object fluid so that a first temperature detected signal is produced;
   a downstream temperature sensor arranged downstream of the object fluid with respect to the heater to detect the temperature of the object fluid so that a second temperature detected signal is produced;
   a side temperature sensor arranged in a direction orthogonal to the flow direction of the object fluid with respect to the heater and located on a side of the heater not upstream and not downstream of the object fluid with respect to the heater, to detect the temperature of the object fluid so that a third temperature detected signal is produced;
   a supporting board for supporting the heater, the upstream sensor, the downstream sensor and the side temperature sensor; and
   flow rate measuring means for measuring a flow rate of the object fluid on the basis of a difference signal between the first temperature detected signal supplied from the upstream temperature sensor and the second temperature detected signal supplied from the downstream temperature sensor.

25. A flow sensor according to claim 24, wherein two side temperature sensors are arranged on both sides of the heater in a direction orthogonal to the flow direction of the object fluid.

26. A flow sensor according to claim 24, wherein the supporting board has a diaphragm whose periphery is fixed, and the heater, the upstream temperature sensor, the downstream temperature sensor and the side temperature sensor are formed on the diaphragm.

27. A flow sensor according to claim 24, wherein the upstream sensor and the downstream temperature sensors are a thermopile, respectively.

28. A flow sensor according to claim 24, wherein the upstream sensor and the downstream temperature sensors are resistors.

29. A flow sensor according to claim 24, wherein the side temperature sensor is a thermopile.

30. A flow sensor according to claim 24, wherein the side temperature sensor is a resistor.

31. A fluid discriminating apparatus for discriminating the kind of the object fluid using the thermal fluid sensor set forth in claim 24, comprising:

reference value storage means for storing a plurality of kinds of reference values of the third temperature detected signal supplied from the side temperature sensor within the thermal fluid sensor, the reference values corresponding to flow rates of the object fluid flowing through the flow path;

reference value inferring means for inferring a single reference value corresponding to the flow rate of the object fluid measured by the flow rate measuring means from the plurality of kinds of reference values stored in the reference value storage means; and temperature detected signal ratio computing means for computing a ratio of the reference value inferred by the reference value inferring means to the third temperature detected signal supplied from the side temperature sensor, wherein the fluid property computing means computes the property of the object fluid on the basis of the ratio computed by the temperature detected signals ratio computing means.

32. A fluid discriminating apparatus according to claim 24, flow rate measuring means for measuring a flow rate of the object fluid on the basis of a difference signal between the first temperature detected signal supplied from the upstream temperature sensor and the second temperature detected signal supplied from the downstream temperature sensor; and fluid property computing means for multiplying the flow rate or its square root of the object fluid flowing through the flow path measured by the flow rate measuring means by the temperature detected signal supplied from the side temperature sensor in the flow sensor, thereby acquiring the property of the object fluid.

33. A fluid discriminating apparatus according to claim 31, further comprising: fluid kind discriminating means for discriminating the kind of the object fluid on the basis of the property of the object fluid.

34. A fluid discriminating apparatus for discriminating the kind of the object fluid using the flow sensor set forth in claim 24, comprising:

flow rate measuring means for measuring a flow rate of the object fluid on the basis of a difference signal between the first temperature detected signal supplied from the upstream temperature sensor and the second temperature detected signal supplied from the downstream temperature sensor; and reference range data storage means for storing data of a plurality of kinds of reference ranges of the third temperature detected signal corresponding flow rates of the object fluid flowing through the flow path, the reference ranges being different according to the kinds of the object fluid and correlated with the kinds;

reference range data inferring means for inferring a single reference range data corresponding to the flow rate of the object fluid from data of the plurality of reference ranges stored in the reference range data storage means;

pertinent reference range determining means for determining the reference range correlated with the object fluid to which the third temperature detected signal belongs, wherein it is determined that the object fluid correlated with the reference range thus determined is the object fluid flowing through the flow path.

35. A fluid discriminating method for discriminating the kind of the object fluid using the flow sensor set force in claim 24, flow rate measuring step of measuring a flow rate of the object fluid on the basis of a difference signal between the first temperature detected signal supplied from the upstream temperature sensor and the second temperature detected signal supplied from the downstream temperature sensor;

reference value storage step of storing a plurality of kinds of reference values of the third temperature detected signal supplied from the side temperature sensor within the flow sensor, the reference values corresponding to flow rates of the object fluid flowing through the flow path;

reference value inferring step of inferring a single reference value corresponding to the flow rate of the object fluid measured by the flow rate measuring means from the plurality of kinds of reference values stored in the reference value storage means; and temperature detected signal ratio computing step of computing a ratio of the reference value inferred by the reference value inferring means to the third temperature detected signal supplied from the side temperature sensor, wherein the fluid property computing means computes the property of the object fluid on the basis of the ratio computed by the temperature detected signal ratio computing means.

36. A fluid discriminating method for discriminating the kind of the object fluid using the flow sensor set force in claim 24, flow rate measuring step for computing a flow rate of the object fluid on the basis of a difference signal between the first temperature detected signal supplied from the upstream temperature sensor and the second temperature detected signal supplied from the downstream temperature sensor; and fluid property computing step of multiplying the flow rate or its square root of the object fluid flowing through the flow path measured by the flow rate measuring means by the temperature detected signal supplied from the side temperature sensor in the flow sensor, thereby acquiring the property of the object fluid.

37. A fluid discriminating method according to claim 35, further comprising: fluid kind discriminating step of discriminating the kind of the object fluid on the basis of the property of the object fluid.

38. A fluid discriminating method for discriminating the kind of the object fluid using the flow sensor set forth in claim 24, comprising:

flow rate measuring step of measuring a flow rate of the object fluid on the basis of a difference signal between the first temperature detected signal supplied from the upstream temperature sensor and the second temperature detected signal supplied from the downstream temperature sensor; and reference range data inferring step of inferring a single reference range data corresponding to the flow rate of the object fluid from data of a plurality kinds of reference ranges the third temperature detected signal corresponding flow rates of the object fluid flowing through the flow path, the reference ranges being different according to the kinds of the object fluid and correlated with the kinds;

pertinent reference range determining step of determining the reference range correlated with the object fluid to which the third temperature detected signal belongs, wherein it is determined that the object fluid correlated with the reference range thus determined is the object fluid flowing through the flow path.

39. A flow rate measuring apparatus for measuring the flow rate of the object fluid flowing through the flow path using the flow sensor set forth in claim 24, comprising:

flow rate computing means computing a flow rate of the object fluid on the basis of a difference signal between the first temperature detected signal supplied from the upstream temperature sensor and the second temperature detected signal supplied from the downstream temperature sensor; and fluid property computing means for computing the property of the object fluid on the basis of the third temperature detected signal supplied from the side temperature sensor with the flow sensor; and flow rate correcting means for correcting the flow rate of the object fluid computed by the flow rate computing means on the basis of the property of the object fluid computed by the fluid property computing means.

40. A flow rate measuring apparatus according to claim 39, wherein the flow rate correcting means produces a flow rate detected signal when the difference signal is divided by the third temperature detected signal, thereby correcting the flow rate measured by the flow rate measuring means.

41. A flow rate measuring apparatus for measuring the flow rate of the object fluid flowing through the flow path using the flow sensor set forth in claim 24, comprising:

flow rate computing means for computing a flow rate of the object fluid on the basis of a difference signal between the first temperature detected signal supplied from the upstream temperature sensor and the second temperature detected signal supplied from the downstream temperature sensor; and deciding means for deciding whether the flow rate of the fluid measured by the flow rate measuring means is in a high flow rate state or a low flow rate;

flow rate outputting means for outputting an output signal from the flow rate measuring means as a flow rate detected signal as it is if the flow rate is decided to be in the low flow rate state, and another output signal when the output signal from the flow rate measuring means is divided by the third temperature detected signal from the side temperature sensor if the flow rate is decided to be in the high flow rate state.

42. A flow rate measuring apparatus for measuring the flow rate of the object fluid flowing through the flow path using the flow sensor set forth in claim 24, comprising:

flow rate computing means for computing a flow rate of the object fluid on the basis of a difference signal between the first temperature detected signal supplied from the upstream temperature sensor and the second temperature detected signal supplied from the downstream temperature sensor and producing an output signal having a value corresponding to the flow rate thus computed;

fluid property computing means for computing the property of the object fluid on the basis of the third temperature detected signal supplied from the side temperature sensor in the flow sensor;

parameter storage means storing a plurality of kinds of parameters each for converting the output signal from the flow rate computing means into a flow rate; and selecting means for selecting a single parameter of the plurality of kinds of parameters stored in the parameter storage means on the basis of the property of the object fluid computed by the fluid property computing means, wherein the flow rate converted from the output signal from the flow rate measuring means using the single parameter selected by the selecting means is taken as the measured value of the flow rate of the object fluid flowing through the flow path.

43. A flow rate measuring method for measuring the flow rate of the object fluid flowing through the flow path using the flow sensor set forth in claim 24, comprising:

flow rate computing step of computing a flow rate of the object fluid on the basis of a difference signal between the first temperature detected signal supplied from the upstream temperature sensor and the second temperature detected signal supplied from the downstream temperature sensor; and fluid property computing step of computing the property of the object fluid on the basis of the third temperature detected signal supplied from the side temperature sensor within the flow sensor;

flow rate correcting step of correcting the flow rate of the object fluid computed by the flow rate computing means on the basis of the property of the object fluid computed in the fluid property computing step.

44. A flow rate measuring method according to claim 43, wherein the flow rate computing step acquires the signal having a value corresponding to the computed flow rate of the object fluid and the flow rate correcting step produces a flow rate detected signal when the difference signal is divided by the third temperature detected signal.

45. A flow rate measuring method for measuring the flow rate of the object fluid flowing through the flow path using the flow sensor set forth in claim 24, comprising:

flow rate computing step for computing a flow rate of the object fluid on the basis of a difference signal between the first temperature detected signal supplied from the upstream temperature sensor and the second temperature detected signal supplied from the downstream temperature sensor, thereby acquiring a signal having the value corresponding to the computed flow rate; and deciding step for deciding whether the flow rate of the fluid acquired in the flow rate measuring step is in a high flow rate state or a low flow rate;

flow rate outputting step for outputting an output signal acquired in the flow rate computing step as a flow rate detected signal as it is if the flow rate is decided to be in the low flow rate state, and another output signal when the output signal acquired in the flow rate computing step is divided by the third temperature detected signal from the side temperature sensor if the flow rate is decided to be in the high flow rate state.

46. A flow rate measuring method for measuring the flow rate of the object fluid flowing through the flow path using the flow sensor set forth in claim 24, flow rate computing step of computing a flow rate of the object fluid on the basis of a difference signal between the first temperature detected signal supplied from the upstream temperature sensor and the second temperature detected signal supplied from the downstream temperature sensor and producing an output signal having a value corresponding to the flow rate thus computed;

fluid property computing step of computing the property of the object fluid on the basis of the third temperature detected signal supplied from the side temperature sensor in the flow sensor;

parameter storage step of storing a plurality of kinds of parameters each for converting the output signal acquired in the flow rate computing step into a flow rate; and selecting step of selecting a single parameter of the plurality of kinds of parameters on the basis of the property of the object fluid computed in the fluid property computing step, wherein the flow rate converted from the output signal from the flow rate computing step using the single parameter selected in the selecting step is taken as the measured value of the flow rate of the object fluid flowing through the flow path.

47. A thermal fluid sensor comprising:

a heater for heating an object fluid for measurement flowing through a flow path by driving current externally supplied;

a side temperature sensor arranged in a direction orthogonal to the flow direction of the object fluid with respect to the heater and located on a side of the heater not upstream and not downstream of the object fluid with respect to the heater, to detect the temperature of the object fluid so that a temperature detected signal to be used to compute the property of the object fluid is produced; and a supporting board for supporting the heater and the side temperature sensor.

48. A flow sensor comprising:

a heater for heating an object fluid for measurement flowing through a flow path by a driving current externally supplied;

an upstream temperature sensor arranged upstream of the object fluid with respect to the heater to detect the temperature of the object fluid so that a first temperature detected signal is produced;

a downstream temperature sensor arranged downstream of the object fluid with respect to the heater to detect the temperature of the object fluid so that a second temperature detected signal is produced, said first and said second temperature detected signals being used to compute the flow rate of the object fluid, a side temperature sensor arranged in a direction orthogonal to the flow direction of the object fluid with respect to the heater and located on a side of the heater not upstream and not downstream of the object fluid with respect to the heater, to detect the temperature of the object fluid so that a third temperature detected signal to be used to compute the property of the object fluid is produced; and a supporting board for supporting the heater, the upstream sensor, the downstream sensor and the side temperature sensor.

* * * * *